US012796962B2

(12) United States Patent
Kanjilal et al.

(10) Patent No.: US 12,796,962 B2
(45) Date of Patent: Nov. 17, 2026

(54) MACHINE LEARNING BASED HUMAN ACTIVITY RECOGNITION SYSTEM AND RELATED METHODS

(71) Applicant: UNIVERSITY OF SOUTH FLORIDA, Tampa, FL (US)

(72) Inventors: Ria Kanjilal, Tampa, FL (US); Ismail Uysal, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 388 days.

(21) Appl. No.: 18/175,423

(22) Filed: Feb. 27, 2023

(65) Prior Publication Data

US 2023/0270353 A1 Aug. 31, 2023

Related U.S. Application Data

(60) Provisional application No. 63/314,347, filed on Feb. 25, 2022.

(51) Int. Cl.
*A61B 5/11* (2006.01)
*A61B 5/00* (2006.01)

(52) U.S. Cl.
CPC .......... *A61B 5/1118* (2013.01); *A61B 5/7267* (2013.01)

(58) Field of Classification Search
CPC ............................ A61B 5/7267; A61B 5/1118
See application file for complete search history.

(56) References Cited

PUBLICATIONS

Mannini, A. et al., Activity Recognition Using a Single Accelerometer Placed at the Wrist or Ankle, Medicine and Science in Sports and Exercise, 2013, 45(11):2193-2203.
Mannini, A. et al., Activity Recognition in Youth Using Single Accelerometer Placed at Wrist or Ankle, Medicine and Science in Sports and Exercise, 2017, 49(4):801-812.

*Primary Examiner* — Alyssa M Alter
(74) *Attorney, Agent, or Firm* — Husch Blackwell LLP

(57) ABSTRACT

Methods and systems for network scanning activity detection are disclosed. Various embodiments of the methods and systems may include: obtaining raw sensor data for a user; generating spectrotemporal representation data corresponding to the raw sensor data; applying the spectrotemporal representation data to a trained deep learning model; receiving a classification indication from the trained deep learning model; and providing a human activity indication of the user based on the classification indication. Other aspects, embodiments, and features are also claimed and described.

17 Claims, 18 Drawing Sheets

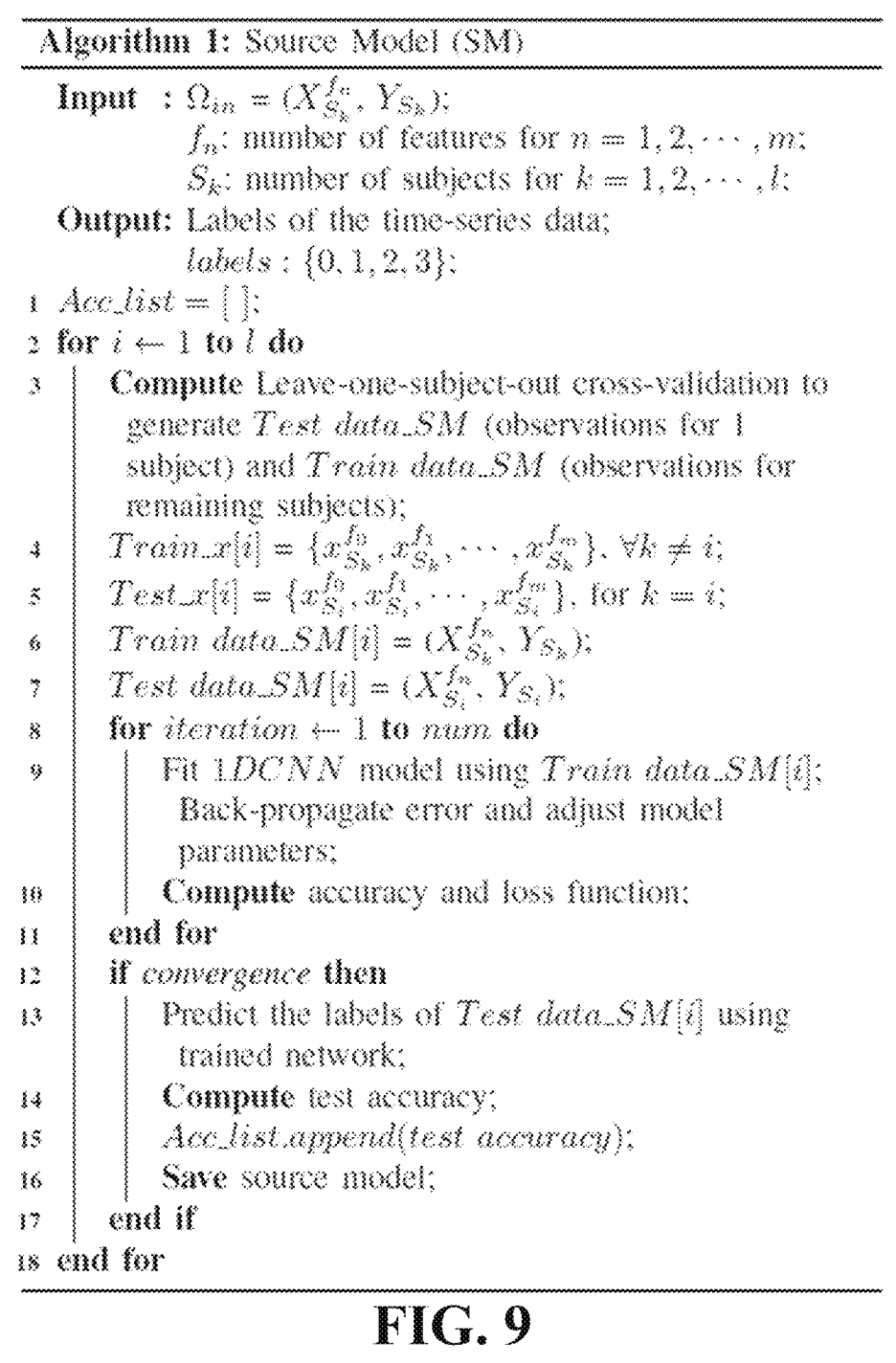

Algorithm 1: Source Model (SM)

Input : $\Omega_{in} = (X_{S_k}^{f_n}, Y_{S_k})$;
$f_n$: number of features for $n = 1, 2, \cdots, m$;
$S_k$: number of subjects for $k = 1, 2, \cdots, l$;
Output: Labels of the time-series data;
$labels : \{0, 1, 2, 3\}$;

$Acc\_list = [\,]$;
for $i \leftarrow 1$ to $l$ do
  Compute Leave-one-subject-out cross-validation to generate $Test\ data\_SM$ (observations for 1 subject) and $Train\ data\_SM$ (observations for remaining subjects);
  $Train\_x[i] = \{x_{S_k}^{f_0}, x_{S_k}^{f_1}, \cdots, x_{S_k}^{f_m}\}, \forall k \neq i$;
  $Test\_x[i] = \{x_{S_i}^{f_0}, x_{S_i}^{f_1}, \cdots, x_{S_i}^{f_m}\}$, for $k = i$;
  $Train\ data\_SM[i] = (X_{S_k}^{f_n}, Y_{S_k})$;
  $Test\ data\_SM[i] = (X_{S_i}^{f_n}, Y_{S_i})$;
  for $iteration \leftarrow 1$ to $num$ do
    Fit $1DCNN$ model using $Train\ data\_SM[i]$; Back-propagate error and adjust model parameters;
    Compute accuracy and loss function;
  end for
  if $convergence$ then
    Predict the labels of $Test\ data\_SM[i]$ using trained network;
    Compute test accuracy;
    $Acc\_list.append(test\ accuracy)$;
    Save source model;
  end if
end for

FIG. 9

Algorithm 2: Sub-transfer Learning Model (STLM)

Input : $\Omega_{in} = (X_{S_k}^{f_n}, Y_{S_k})$;
$f_n$: number of features for $n = 1, 2, \cdots, m$;
$S_k$: number of subjects for $k = 1, 2, \cdots, l$;
Output: Labels of the time-series data;
$labels : \{0, 1, 2, 3\}$;

```
Repeat the steps of the source model;
accuracyList = [ ];
train_size = [10, 25, 50, 75, 90];
for j ← 1 to len(train_size) do
    tr_size = train_size[j];
    if (tr_size == 10)or(tr_size == 90) then
        cross_val = 10;
    end if
    if (tr_size == 25)or(tr_size == 75) then
        cross_val = 4;
    end if
    if (tr_size == 50) then
        cross_val = 2;
    end if
    accList = [ ];
    testx = Test_x[i];
    testy = Test_y[i];
    for tr_id, ts_id in cross_val.split(testx, testy) do
        tr_x, ts_x = testx[tr_id], testx[ts_id];
        tr_y, ts_y = testy[tr_id], testy[ts_id];
        Train_data = [tr_x, tr_y];
        Test_data = [ts_x, ts_y];
        tr_smote = SMOTE(Train_data, N, K);
        // N = 1000: amount of
           oversampling (%), K = 5:
           number of nearest neighbors
           to consider.
        Load source model;
        for iteration ← 1 to num do
            Update source model by training on
             tr_smote in each iteration;
            Compute accuracy and loss function;
        end for
        if convergence then
            Predict the labels of Test_data using
             trained network;
            Compute test_accuracy;
        end if
        accList.append(test_accuracy);
    end for
    Acc = np.array(accList);
    acc_mean = mean(Acc);
    accuracyList.append(acc_mean);
end for
```

FIG. 10

Algorithm 3: Source Model using 2D-CNN Algorithm (SM 2D-CNN)

Input : $\Omega_{kn} = (X^{f_n}_{S_k}, Y_{S_k})$;
$f_n$: number of features for $n = 1, 2, \cdots, m$;
$S_k$: number of subjects for $k = 1, 2, \cdots, l$;
Output: Labels of the time-series data;
$labels : \{0, 1, 2, 3\}$;

Function Spect $(x^{f_n}_{S_k}, y_{S_k})$:
  $\omega_{kn} = [x^{f_n}_{S_k}, y_{S_k}]$;
  $data\_sh = random\_shuffle[\omega_{kn}]$;
  $x1^{f_n}_{S_k} = data\_sh[x^{f_n}_{S_k}]$;
  $y1_{S_k} = data\_sh[y_{S_k}]$;
  ab = [ ];
  for $j \leftarrow 1$ to $len(x1^{f_n}_{S_k})$ do
    Compute spectrogram from $x1^{f_n}_{S_k}$;
    $S = Spectrogram(x1^{f_n}_{S_k}, kaiser(128, 18), 64, 64, 90)$;
    Display $S$, spectrogram image as (13, 13) dimension;
    $t_1 = absolute(S(1:13, 1:13))$;
    $ab.append(t_1)$;
  end for
  $sp = np.array(ab)$;
  return $(sp, y1_{S_k})$ $[spect, dY_{S_k}] = Spect(X^{f_n}_{S_k}, Y_{S_k})$;
// Calling the function *'Spect'* to generate spectrogram representations of 1D data.
for $i \leftarrow 1$ to $l$ do
  Compute Leave-one-subject-out cross-validation to generate *Test data_SM* (observations for 1 subject) and *Train data_SM* (observations for remaining subjects);
  $Train\_x[i] = spect[k\ != i], \forall k \neq i$;
  $Test\_x[i] = spect[k == i]$, for $k = i$;
  $Train\ data\_SM[i] = (Train\_x[i], dY_{S_k}), \forall k \neq i$;
  $Test\ data\_SM[i] = (Test\_x[i], dY_{S_k})$, for $k = i$;
  for $iteration \leftarrow 1$ to $num$ do
    Fit $2DCNN$ model using $Train\ data\_SM[i]$; Perform convolution and pooling operations; Back-propagate error and adjust model parameters;
    Compute accuracy and loss function;
  end for
  if *convergence* then
    Predict the labels of $Test\ data\_SM[i]$ using trained network;
    Compute test accuracy;
    Save source model;
  end if
end for

FIG. 11

Algorithm 4: Sub-transfer Learning Model using 2D-CNN Algorithm (STLM 2D-CNN

```
Input  : Ω_tss = (X_{S_k}^{f_n}, Y_{S_k});
         f_n: number of features for n = 1, 2, ··· , m;
         S_k: number of subjects for k = 1, 2, ··· , l;
Output: Labels of the time-series data:
         labels : {0, 1, 2, 3};
Repeat the steps of the source model for 2DCNN;
accuracyList = [ ];
train_size = [10, 25, 50, 75, 90];
for j ← 1 to len(train_size) do
    tr_size = train_size[j];
    if (tr_size == 10)or(tr_size == 90) then
        cross_val = 10;
    end if
    if (tr_size == 25)or(tr_size == 75) then
        cross_val = 4;
    end if
    if (tr_size == 50) then
        cross_val = 2;
    end if
    accList = [ ];
    testx = Test_x[i];
    testy = Test_y[i];
    for tr_id, ts_id in cross_val.split(testx, testy) do
        tr_x, ts_x = testx[tr_id], testx[ts_id];
        tr_y, ts_y = testy[tr_id], testy[ts_id];
        Train_data = [tr_x, tr_y];
        Test_data = [ts_x, ts_y];
        tr_smote = SMOTE(Train_data, N, K);
        // N = 1000: amount of
           oversampling (%), K = 5:
           number of nearest neighbors
           to consider.
        [sp_tr, y_tr] = Spect(tr_smote_x, tr_smote_y);
        [sp_ts, y_ts] = Spect(ts_x, ts_y);
        // Calling the function 'Spect' to
           generate spectrogram
           representations of 1D tr_smote
           data and Test_data.
        Load source model for 2DCNN;
        for iteration ← 1 to num do
            Update source model for 2DCNN by
             training on tr_smote in each iteration;
            Compute accuracy and loss function;
        end for
        if convergence then
            Predict the labels of Test_data using
             trained network;
            Compute test_accuracy;
        end if
        accList.append(test_accuracy);
    end for
    Acc = np.array(accList);
    acc_mean = mean(Acc).
    accuracyList.append(acc_mean);
end for
```

FIG. 12

MACHINE LEARNING BASED HUMAN ACTIVITY RECOGNITION SYSTEM AND RELATED METHODS

CROSS-REFERENCE TO RELATED APPLICATION(S)

This application is based on, claims priority to, and incorporates herein by reference in their entirety U.S. Provisional Application Ser. No. 63/314,347, filed Feb. 25, 2022.

STATEMENT REGARDING FEDERALLY SPONSORED RESEARCH

N/A

BACKGROUND

Advances in healthcare and related disciplines create both improved outcomes for patients, as well as an increasing need for data regarding disease trends and associated risk factors, outcomes, treatment methods, and pattern of care by continuous monitoring of patients' health, medical costs, etc. A recent projection relating to disease trends in the United States found that diabetes will increase by 54% to include more than 54.9 million Americans by 2030. Another study predicted that nearly one in every four adults will have severe obesity by 2030 and the prevalence will be higher than 25% in twenty-five states. To combat this potentially-significant increase in diseases and risk factors, additional data and monitoring are desirable. Such data and monitoring can both assist individuals in recognizing how they can improve their health, as well as helping provide better data to health care professionals about the daily lives of their patients.

In this regard, the inventors believe that continuous monitoring and recognition of daily physical activities can reduce the risk of chronic diseases including diabetes, obesity and associated cardiovascular problems. However, patient tolerance for invasive sensors and/or requirements for manual data entry would not allow for conventional patient data acquisition to be pervasive enough. Thus, the inventors recognize that a need exists for a simple, effective, and unobjectionable system to collect data on human activity, that patients can utilize in their daily lives.

SUMMARY

The following presents a simplified summary of one or more aspects of the present disclosure, to provide a basic understanding of such aspects. This summary is not an extensive overview of all contemplated features of the disclosure and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

In some aspects of the present disclosure, methods, systems, and apparatus for human activity recognition are disclosed. These methods, systems, and apparatus may include steps or components for: obtaining raw sensor data for a user; generating spectrotemporal representation data corresponding to the raw sensor data; applying the spectrotemporal representation data to a trained deep learning model; receiving a classification indication from the trained deep learning model; and providing a human activity indication of the user based on the classification indication.

In further aspects of the present disclosure, methods, systems, and apparatus for human activity detection training are disclosed. These methods, systems, and apparatus may include steps or components for: obtaining a plurality of raw sensor training datasets; generating a plurality of spectrotemporal representation training datasets based on the plurality of raw sensor training datasets; and training a deep learning model based on the plurality of spectrotemporal representation training datasets to classify the plurality of spectrotemporal representation training datasets into a plurality of classification indications.

These and other aspects of the disclosure will become more fully understood upon a review of the drawings and the detailed description, which follows. Other aspects, features, and embodiments of the present disclosure will become apparent to those skilled in the art, upon reviewing the following description of specific, example embodiments of the present disclosure in conjunction with the accompanying figures. While features of the present disclosure may be discussed relative to certain embodiments and figures below, all embodiments of the present disclosure can include one or more of the advantageous features discussed herein. In other words, while one or more embodiments may be discussed as having certain advantageous features, one or more of such features may also be used in accordance with the various embodiments of the disclosure discussed herein. Similarly, while example embodiments may be discussed below as devices, systems, or methods embodiments it should be understood that such example embodiments can be implemented in various devices, systems, and methods.

BRIEF DESCRIPTION OF THE DRAWINGS

FIG. 9 illustrates an example source model (SM) algorithm for a 1D-CNN model according to some embodiments.

FIG. 10 illustrates an example sub-transfer learning model (STLM) algorithm for a 1D-CNN model according to some embodiments.

FIG. 11 illustrates an example source model (SM) algorithm for a 2-CNN model according to some embodiments.

FIG. 12 illustrates an example sub-transfer learning model (STLM) algorithm for a 2D-CNN model according to some embodiments.

DETAILED DESCRIPTION

The detailed description set forth below in connection with the appended drawings is intended as a description of various configurations and is not intended to represent the only configurations in which the subject matter described herein may be practiced. The detailed description includes specific details to provide a thorough understanding of various embodiments of the present disclosure. However, it will be apparent to those skilled in the art that the various features, concepts and embodiments described herein may be implemented and practiced without these specific details. In some instances, well-known structures and components are shown in block diagram form to avoid obscuring such concepts.

Example Human Activity Recognition System

Figure 1:
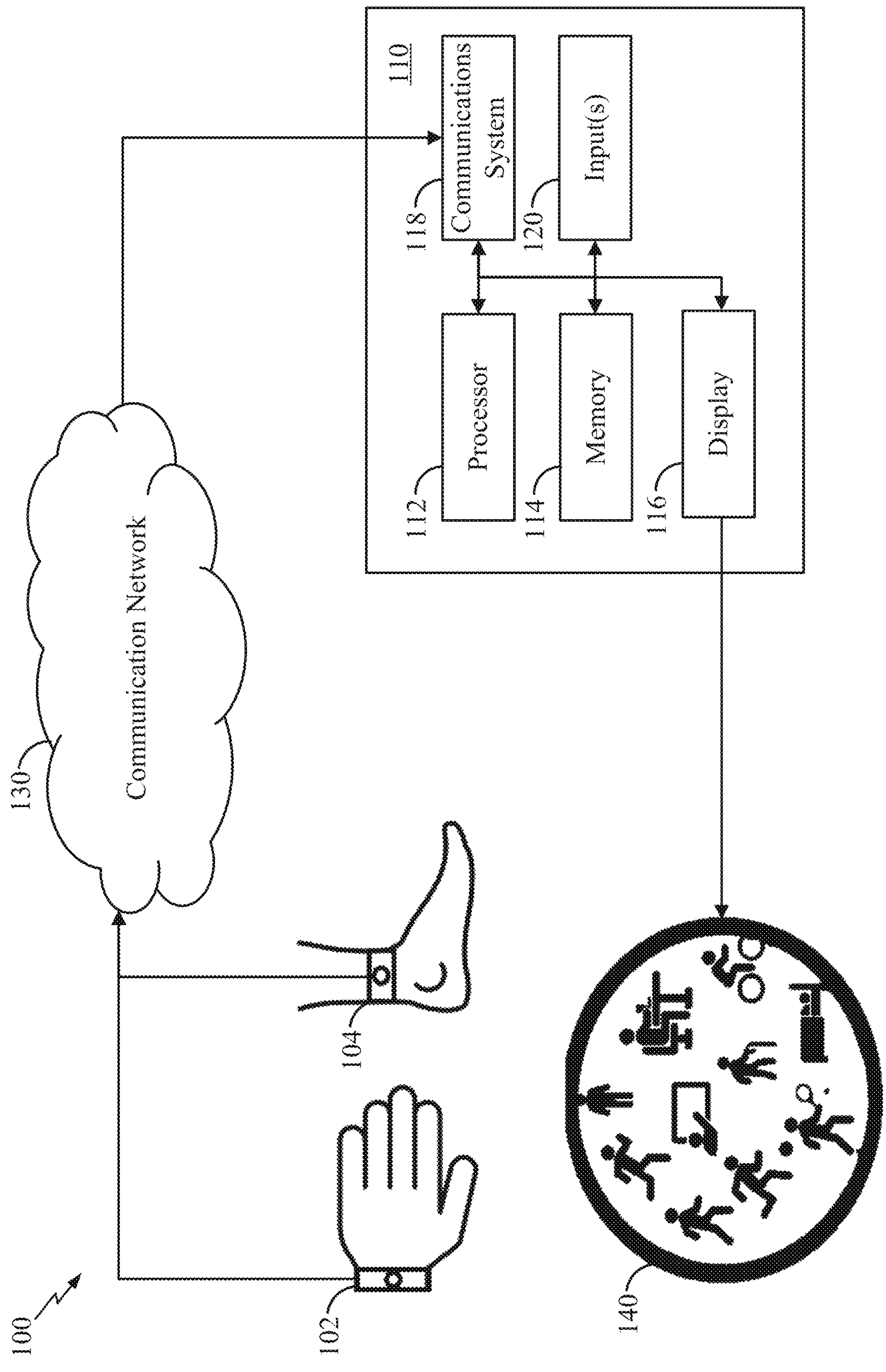
FIG. 1 is a block diagram conceptually illustrating a system for network scanning activity detection according to some embodiments.

FIG. 1 shows a block diagram illustrating a system for human activity recognition according to some embodiments. In some examples, computing device 110 can obtain or receive raw sensor data from one or more motion sensors 102, 104, generate spectrotemporal representation data corresponding to the raw sensor data, apply the spectrotemporal representation data to a trained machine learning model, receive a classification indication from the trained deep learning model, and provide a human activity indication of the user based on the classification indication. In further examples, computing device 110 can obtain or receive raw sensor training datasets from one or more motion sensors 102, 104, generate multiple spectrotemporal representation training datasets based on the raw sensor training datasets, and train a deep learning model based on the multiple spectrotemporal representation training datasets to classify the multiple spectrotemporal representation training datasets into multiple classification indications.

In some examples, the raw sensor data can be produced by one or more motion sensors (e.g., smart wrist band 102, smart ankle band 104, a cell phone, an accelerometer, a gyroscope, an inertial measurement unit (IMU) device, any other suitable sensors). However, it should be appreciated that computing device 110 can receive the raw sensor data, which is stored in a database, via communication network 130 and communications system 118 of computing device 110. In further examples, the one or more motion sensors can be part of computing device 110 and directly provide raw sensor data to processor 112.

In further examples, computing device 110 can include processor 112 can include processor 112. In some embodiments, the processor 112 can be any suitable hardware processor or combination of processors, such as a central processing unit (CPU), a graphics processing unit (GPU), an application specific integrated circuit (ASIC), a field-programmable gate array (FPGA), a digital signal processor (DSP), a microcontroller (MCU), etc.

In further examples, computing device 110 can further include a memory 114. The memory 114 can include any suitable storage device or devices that can be used to store suitable data (e.g., raw sensor data, spectrotemporal representation data, machine learning model, etc.) and instructions that can be used, for example, by the processor 112 to obtain raw sensor data for a user; generating spectrotemporal representation data corresponding to the raw sensor data; apply the spectrotemporal representation data to a trained deep learning model; receive a classification indication from the trained deep learning model; provide a human activity indication of the user based on the classification indication; obtain a plurality of raw sensor training datasets; generate a plurality of spectrotemporal representation training datasets based on the plurality of raw sensor training datasets; train a deep learning model based on the plurality of spectrotemporal representation training datasets to classify the plurality of spectrotemporal representation training datasets into a plurality of classification indications; and fine-tune the trained deep learning model based on the spectrotemporal representation data for the user. The memory 114 can include any suitable volatile memory, non-volatile memory, storage, or any suitable combination thereof. For example, memory 114 can include random access memory (RAM), read-only memory (ROM), electronically-erasable programmable read-only memory (EEPROM), one or more flash drives, one or more hard disks, one or more solid state drives, one or more optical drives, etc. In some embodiments, the processor 112 can execute at least a portion of process 200 or 300 described below in connection with FIG. 2 or 9.

In further examples, computing device 110 can further include communications system 118. Communications system 118 can include any suitable hardware, firmware, and/or software for communicating information over communication network 140 and/or any other suitable communication networks. For example, communications system 118 can include one or more transceivers, one or more communication chips and/or chip sets, etc. In a more particular example, communications system 118 can include hardware, firmware and/or software that can be used to establish a Wi-Fi connection, a Bluetooth connection, a cellular connection, an Ethernet connection, etc.

In further examples, computing device 110 can receive or transmit information (e.g., raw sensor from one or more motion sensor 102, 104, a human activity indication, etc.) and/or any other suitable system over a communication network 130. In some examples, the communication network 130 can be any suitable communication network or combination of communication networks. For example, the communication network 130 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, NR, etc.), a wired network, etc. In some embodiments, communication network 130 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

In further examples, computing device 110 can further include a display 116 and/or one or more inputs 120. In some embodiments, the display 116 can include any suitable display devices, such as a computer monitor, a touchscreen, a television, an infotainment screen, etc. to display the report, the human activity indication 140, or any suitable result of human activity recognition. In further embodiments, the input(s) 120 can include any suitable input devices (e.g., a keyboard, a mouse, a touchscreen, a microphone, etc.) and/or the one or motion sensors 102, 104 that can produce the raw sensor data.

Example Human Activity Recognition Process

Figure 2:
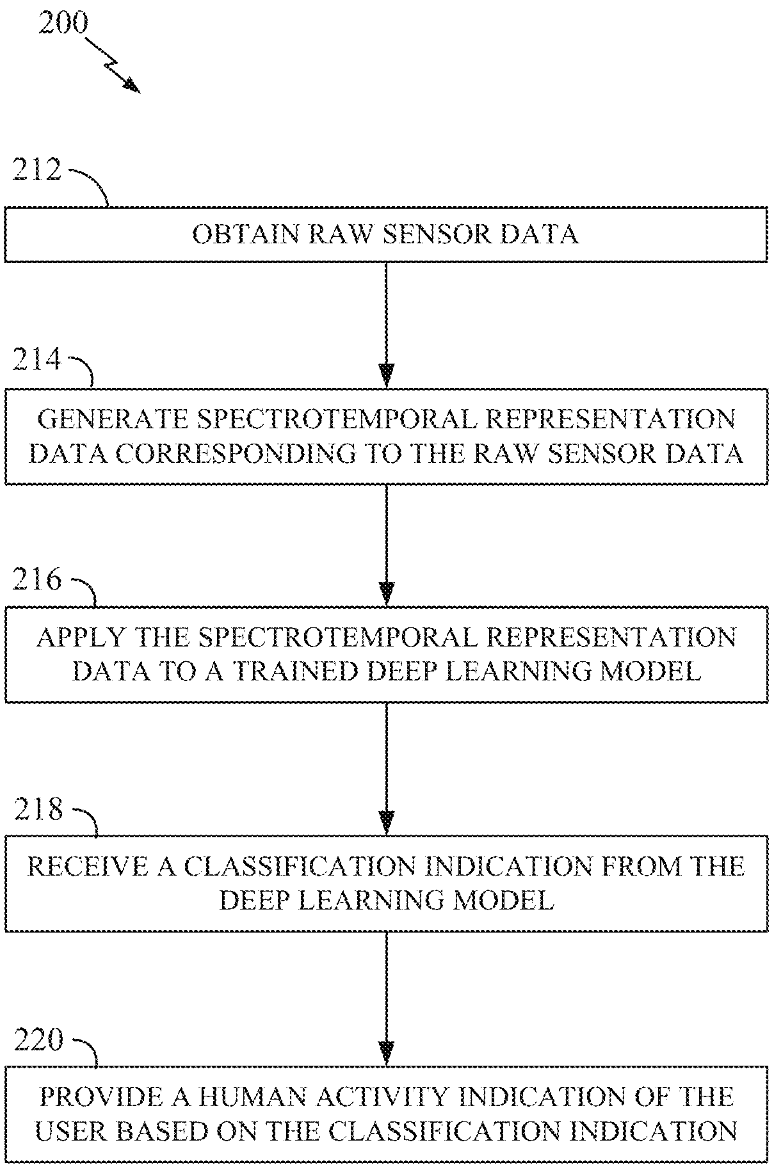
FIG. 2 is a flow diagram illustrating an example process for human activity recognition according to some embodiments.

FIG. 2 is a flow diagram illustrating an example process 200 for human activity recognition in accordance with some aspects of the present disclosure. As described below, a particular implementation can omit some or all illustrated features/steps, may be implemented in some embodiments in a different order, and may not require some illustrated features to implement all embodiments. In some examples, an apparatus (e.g., computing device 110, processor 112 with memory 114, etc.) in connection with FIG. 1 can be used to perform example process 200. However, it should be appreciated that any suitable apparatus or means for carrying out the operations or features described below may perform process 200.

At step 212, process 200 can obtain raw sensor data. In some examples, the raw sensor data can be obtained from one or more motion sensors. The one or more motion sensors can be an accelerometer, a gyroscope, an inertial measurement unit (IMU), and/or any other suitable sensor. In some examples, the one or more motion sensors can be attached on one or both wrists of a user, one or more ankles of the user, and/or any other suitable body part of the user to detect the activity of the user. In other examples, the one or more motion sensors can be equipped in a hand-held smart device (e.g., a cell phone). Although the hand-held device might not be necessarily attached on a body part of the user, the hand-held smart device can also produce raw sensor data indicative of user movement. For example, the user can wear one or two smart wrist bands, one or two smart ankle bands, and/or the hand-held smart device for process 200 to obtain the raw sensor data.

In further examples, the raw sensor data can include accelerometer sensor data, gyroscope sensor data, and/or data combining the accelerometer sensor data and the gyroscope sensor data. In further examples, the raw sensor data can include one-dimensional temporal data. For example, the raw sensor data can include a single-axis temporal acceleration data for one of the three axes (x, y, or z), which happens to demonstrate the biggest dynamic range of motion as the dominant axis.

In further examples, the raw sensor data can include one of multiple age-group sensor data. For example, the raw sensor data can be adult sensor data or youth sensor data. In some examples, adult sensor data are for data collected from people who are equal to or older than a predetermined age (e.g., 15 years old, 18 years old, or any other suitable age) while youth sensor data are for data collected from people who are younger than the predetermined age. Of course, the number of groups can be more than two (e.g., adult and youth). For example, the number of groups can be Group 1 (age 11-20), Group 2 (age 21-30), Group 3 (age 31-40), Group 4 (age 41-50), Group 5 (age 51-60), Group 6 (age 61-70), and/or Group 7 (age 71-80). In further examples, the raw sensor data can include a combination of the age group and location of sensors. For example, the raw sensor data can be one or two groups: adult and youth. Further, the raw sensor data can include ankle sensor data, wrist sensor data, or a combination of the wrist and ankle sensor data.

Figure 3:
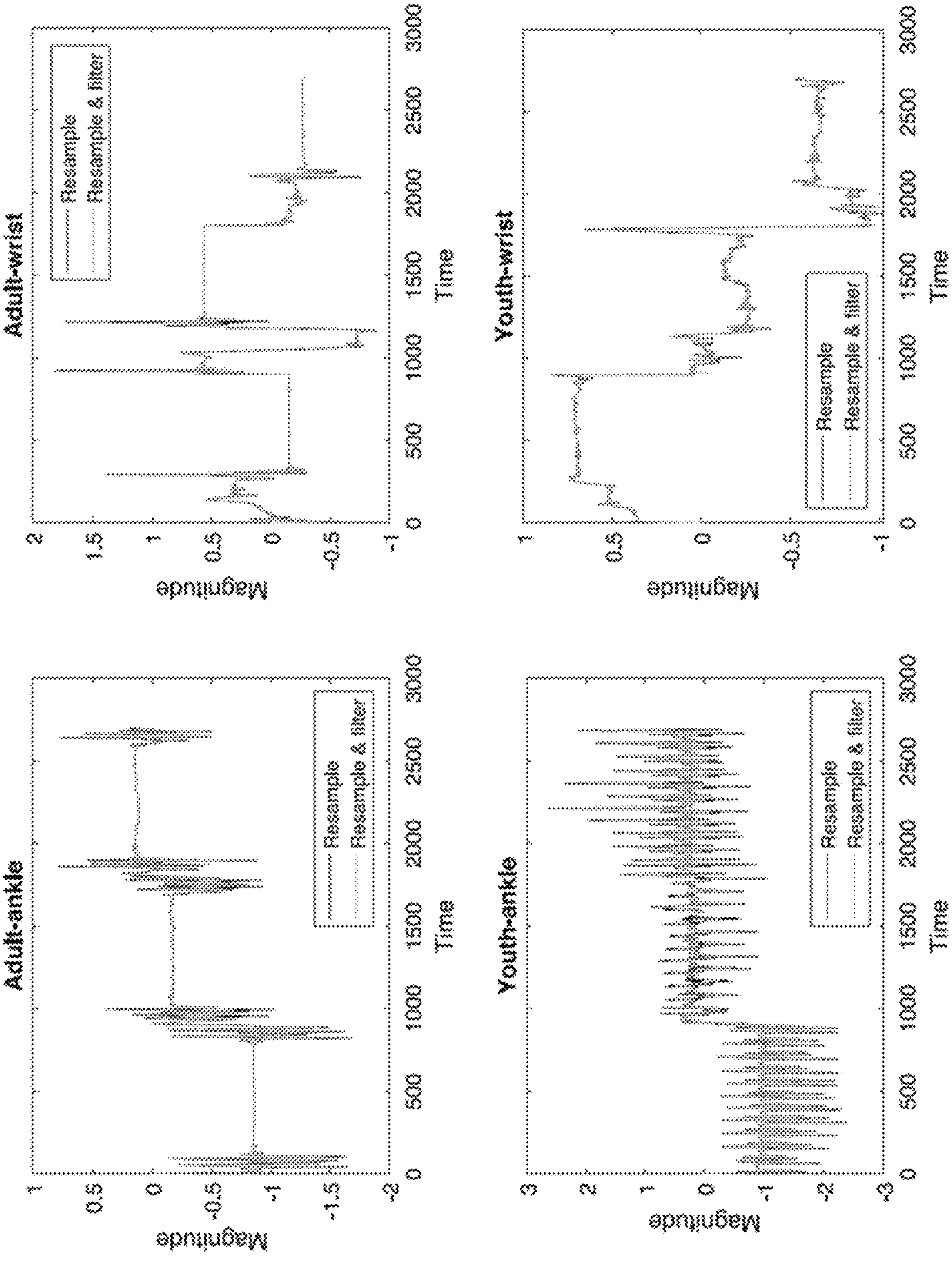
FIG. 3 illustrates an example of resampled and filtered signals according to some embodiments.

In further examples, process 200 can obtain the raw sensor data stored in a database. In further examples, process 200 can preprocess the raw sensor data. For example, the raw sensor data can be non-uniformly sampled data. In the scenario, process 200 can re-sample the non-uniformly sampled data with a uniform fixed rate. For example, the raw sensor data can be resampled (e.g., at 900 samples per second) and filtered using a suitable filter (e.g., a 4th order lowpass digital Butterworth filter) with a suitable cut-off frequency (e.g., at 15 Hz) and a suitable sampling rate (e.g., at 90 Hz) to limit the bandwidth and eliminate non-motion like noise in the raw data. FIG. 3 shows some example observations of resampled and filtered signals.

Raw sensor data may include an output obtained directly from a sensor (such as an analog or digital output of an accelerometer). In other embodiments, raw sensor data may include output of a sensor that has been transformed in format (e.g., digitized, packetized, transmitted via wired or wireless connection, reformatted to a different data object type, etc.), but not substantively altered. For example, raw sensor data may include data that a local controller obtains from an output of an accelerometer, and packetizes for transmission to another processor or database via a specified protocol. However, the raw sensor data in such example has not been upsampled, downsampled, filtered, undergone a domain change (e.g., time to frequency), or otherwise modified from a standpoint of the values represented by the data.

Figure 4:
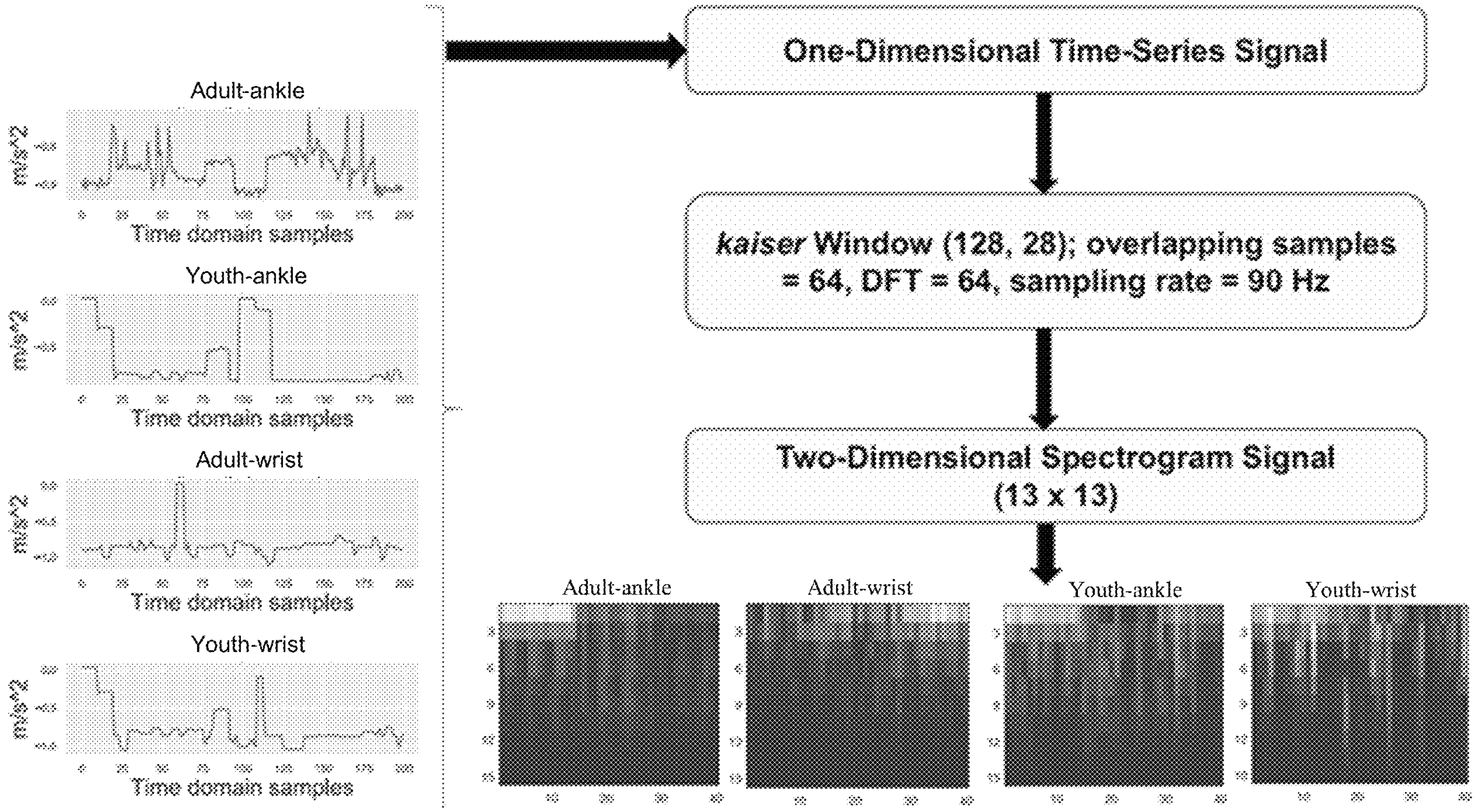
FIG. 4 illustrates an example process to transform one-dimensional time domain signal to two-dimensional frequency domain representation according to some embodiments.
Figure 5:
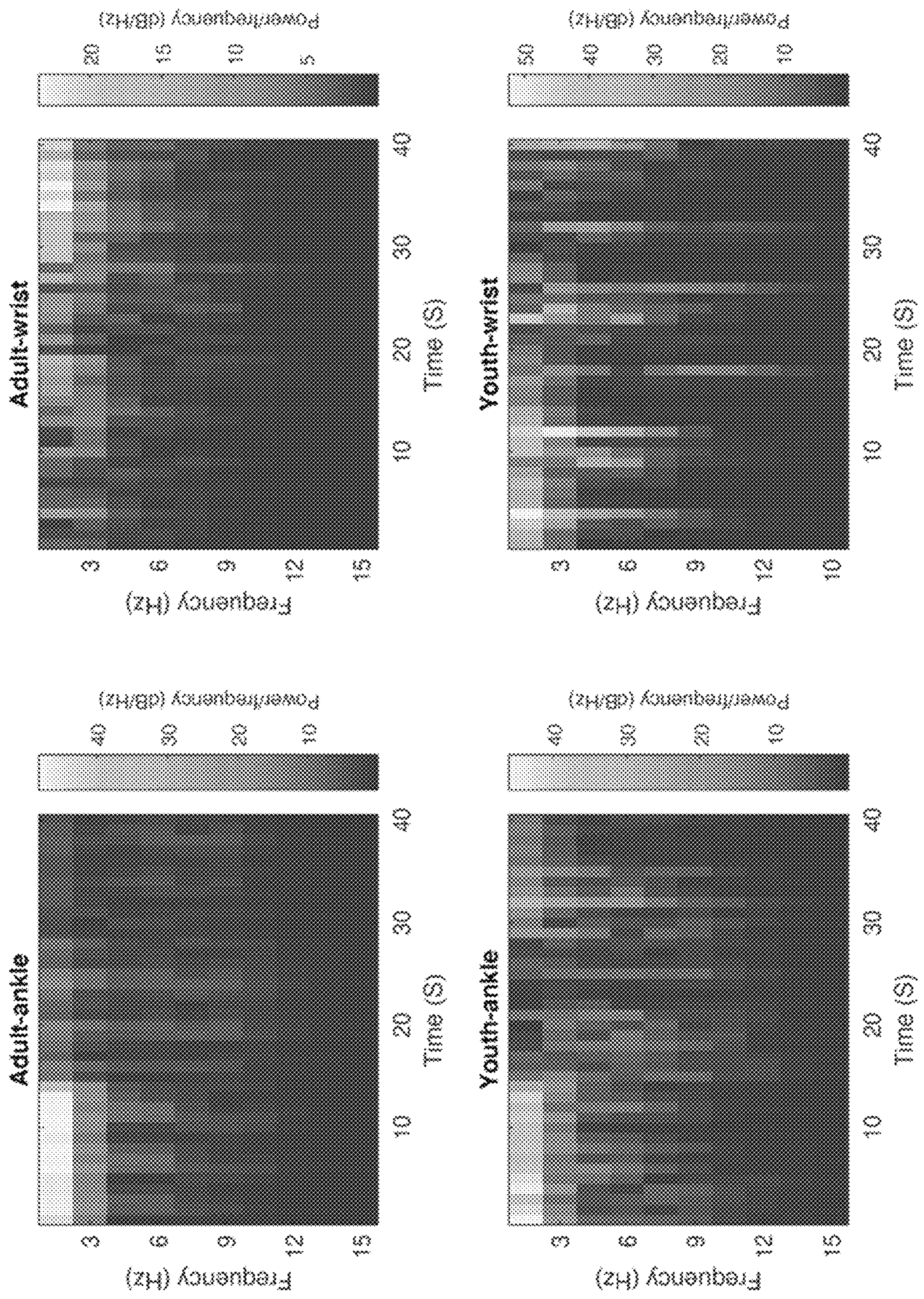
FIG. 5 illustrates an example frequency domain representation of sample observations from the four example raw sensor data datasets according to some embodiments.

At step 214, process 200 can generate spectrotemporal representation data corresponding to the raw sensor data. In some examples, the spectrotemporal representation data can include two-dimensional frequency domain representation data. In further examples, the spectrotemporal representation data can include two-dimensional spectrogram data. In some examples, FIG. 4 shows an example process to transform one-dimensional time domain signal to two-dimensional frequency domain representation. For example, the raw sensor data, which is one-dimensional temporal data, can be transformed into two-dimensional frequency domain representation considering a 'kaiser' window with a suitable vector size (e.g., as (128, 18)), which divides the input into segments of equal size and activate the window operation. Overlapping samples (e.g., 64 overlapping samples) can be used between the adjoining segments to compute a multi-point discrete Fourier Transform (e.g., a 64-point discrete Fourier Transform) where the sampling rate is set at a suitable frequency (e.g., 90 Hz). FIG. 5 shows an example frequency domain representation of sample observations from the four example raw sensor data datasets.

Figure 6:
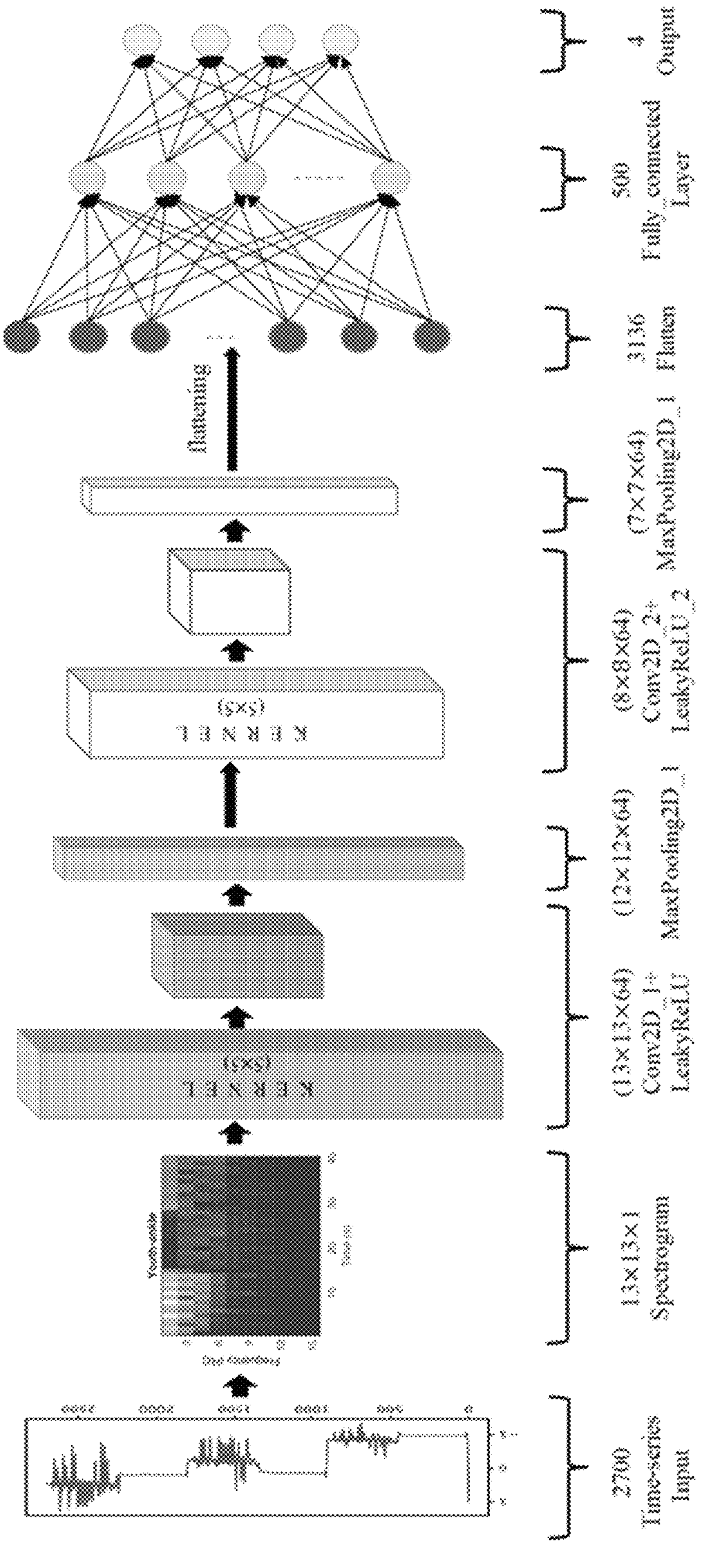
FIG. 6 illustrates an example framework of a two-dimensional convolutional neural network (2D-CNN) model and feature learning using the 2D-CNN model according to some embodiments.

At step 216, process 200 can apply the spectrotemporal representation data to a trained deep learning model. In some examples, the trained deep learning model comprises a two-dimensional convolutional neural network (2D-CNN) model. FIG. 6 illustrates an example framework of the 2D-CNN model and feature learning using the 2D-CNN model. In further examples, the 2D-CNN model comprises: a first two-dimensional convolution layer with a first activation function and a second two-dimensional convolution layer with a second activation function to extract a feature map. In further examples, each of the first two-dimensional convolution layer with the first activation function and the second two-dimensional convolution layer with the second activation function performs a convolution operation with 64 filters of kernel size of (5, 5). In further examples, the 2D-CNN model further comprises: a first max pooling layer and a second max pooling layer to compute maximum information from the feature map, the first max pooling layer being between the first two-dimensional convolution layer with the first activation function and the second two-dimensional convolution layer with the second activation function, a second max pooling layer being coupled with the second two-dimensional convolution layer with the second activation function. In further examples, each of the first max pooling layer and the second max pooling layer has a pool size of (2, 2) and stride of 1. In further examples, the 2D-CNN model further comprises: a fully connected layer configured to receive the maximum information from the feature map; and an output layer coupled to the fully connected layer, the output layer being configured to produce the classification indication. In further examples, the fully connected layer comprises 500 neurons.

In some examples, a two-dimensional convolutional neural network automatically learns rich feature-information from a 2D input representation to provide high classification accuracy. In a time-series classification task, the one-dimensional data naturally needs to be transformed into a 2D representation before utilizing a 2D-CNN. In some examples, process 200 generates spectrogram images from the sensor data, which can model one or both of time and frequency fluctuations in the signals.

In a 2D-CNN, the input data is a matrix or tensor with a 3D spatial structure, where (H, W), (H', W'), and (H", W") represent the size of the spatial dimension of input data, convolution kernel, and output data, respectively. The number of convolution kernel feature channels is represented by D, and D" represents the 3D data.

$x \in \mathbb{R}^{H \times W \times D}$ $f \in \mathbb{R}^{H' \times W' \times D \times D''}$, where x is the input data, f is the convolution filter, and $y \in \mathbb{R}^{H'' \times W'' \times D''}$ y is the output data. The 1D signal x is convoluted by filter f to calculate signal y as follows:

$$y_{i''j''d''} = b_{d''} + \sum_{i'=1}^{H'} \sum_{j'=1}^{W'} \sum_{d'=1}^{D'} f_{i''j''d''} \times x_{i''+i'-1, j''+j'-1, d', d''}.$$

This equation states that $b_{d''}$ is the neuron offset and $f_{i''j''d''}$ is the convolution kernel matrix of the $d^{th}$ i'×j' ($i'^{th}$ neuron and $j'^{th}$ connection).

The pooling layer performs max pooling operation which calculates the maximum response of each feature channel in the H'×W' region.

$$y_{i''j''d''} = \max_{1 \le i' \le H', 1 \le j' \le W'} x_{i''+i'-1, j''+j'-1, d}.$$

In some examples, 1D data is first transformed into spectrogram images of dimension (13×13) and applied as input to the convolution layers. Referring again to FIG. 5, the spectrograms of representative samples from the adult-ankle, adult-wrist, youth-ankle and youth-wrist datasets are shown respectively. One-dimensional temporal data is transformed into two-dimensional frequency domain representation considering a 'kaiser' window with vector size as (128,18) which divides the input into segments of equal size and activates the window operation. 64 overlapping samples are used between the adjoining segments to compute a 64-point discrete Fourier Transform where the sampling rate is set at 90 Hz.

Referring again to FIG. 6, a framework of the specific 2D-CNN model is shown using youth-ankle dataset where two 2D convolution layers with 'LeakyReLU' activation functions perform the convolution operation with 64 filters of kernel size as (5, 5) to extract the feature map. Here, two max pooling layers with pool size (2, 2) and stride=1 compute the maximum information from the feature map. After the pooling operation, the output is flattened and passed to a single fully connected layer of 500 neurons. In some examples, two convolutional layers along with a dropout layer (probability=0.5) reduce the dimension of the input time-series or spectrotemporal data and extract the unsupervised features by adding a pooling layer of size 2. After the pooling operation, the output is flattened and passed through a single fully connected layer with 500 hidden neurons. In some examples, each of the two convolutional layers has a kernel size of (5, 5). The output layer with the 'Softmax' activation function predicts the class labels (i.e., classification indications) for the multiple daily activities (e.g., 4 categorical activities or any other suitable number of activities).

Figure 7:
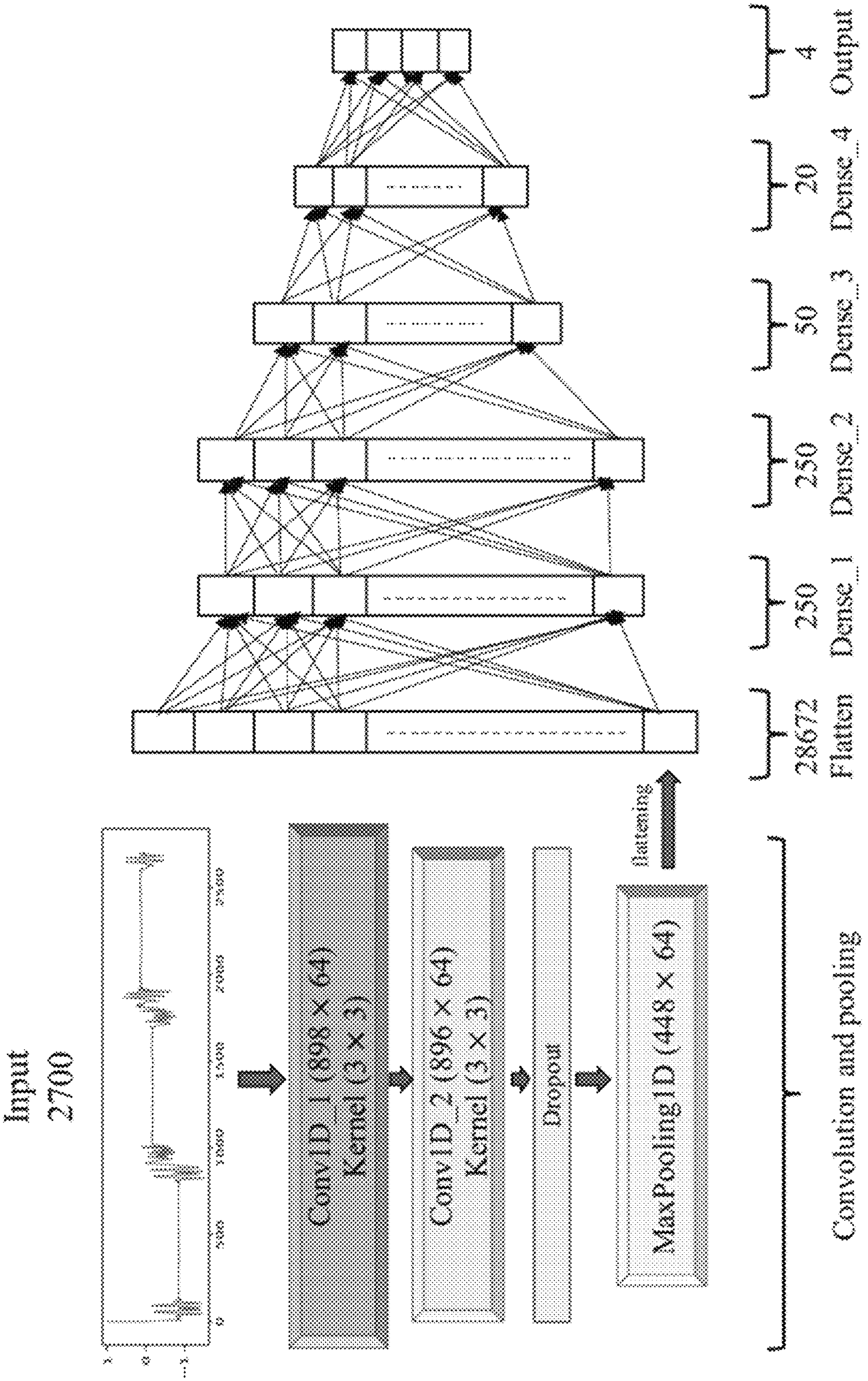
FIG. 7 illustrates an example framework of a one-dimensional convolutional neural network (1D-CNN) model and feature learning using the 1D-CNN model according to some embodiments.

In other examples, process 200 can use one-dimensional convolutional neural network (1D-CNN) rather than the 2D-CNN to receive the classification indication from the trained deep learning model. FIG. 7 illustrates an example framework of a one-dimensional convolutional neural network (1D-CNN) model and feature learning using the 1D-CNN model. When the trained deep learning model is the 1D-CNN, process 200 can skip step 214 and directly apply the raw sensor data, which is one-dimensional time series data, to the trained deep learning model.

In time-series classification with feature learning, 1D-CNN provides a high classification rate with lesser computational complexity compared to other topologies. 1D-CNN uses one-dimensional convolution of the input signal via kernels to extract specific characteristics from the raw signals. The architecture of a 1D-CNN combines the two major tasks, namely feature mapping and prediction of a 1D signal into a single learning system. The input layer receives the raw 1D signal which is forwarded to the convolutional layers. The convolution layers are used for feature mapping from the input, where every convolution layer consists of multiple kernels of the same size, followed by the pooling layer. Pooling performs average or max pooling operations to reduce the size of the input space to help speed up the training process and then send the output to the fully connected layers for conventional input-output mapping. Mathematically, if l is a convolution layer:

$$x_j^l = f\left(\sum_{i=1}^{M} x_i^{l-1} \circledast k_{ij}^l + b_{ij}^l\right),$$

where k represents the convolution kernels, j denotes the number of kernels, M represents the channel number of the input $x^{l-1}$, b is the bias corresponding to the kernel, $f(\ )$ is the activation function and $\circledast$ is the convolution operator.

Referring again to FIG. 7, the deep 1D-CNN architecture is shown for the adult-ankle dataset with 10080 observations in 2700 dimensions to be fed into the model as input. Two 1D-convolutional layers with 64 filters of kernel size (3, 3) perform the forward-backward operation by adjusting the layer-weights and extract the features to provide a high classification rate with lesser complexity. Here, a Dropout' layer with probability=0.5 has also been added to prevent the overfitting of the training process. After the convolution layer, a pooling layer (of size 2) performs max pooling operation which is used to process each feature map to reduce the data dimensionality from 28672 to 448 by selecting the maximum parameters within the range of the predetermined window as the output value. The 1D-CNN model includes 4 fully connected layers 250, 250, 50, 20 neurons respectively to map the output from the convolutional layers into the predicted class labels.

At step 218, process 200 can receive a classification indication from the trained deep learning model. In some examples, the classification indication is one of four classification indications (e.g., corresponding to an ambulation indication, a cycling indication, a sedentary indication, an others indication). However, it should be appreciated that the classification indication can be on of less than or more than four classification indications configured to be determined based on the training process.

At step 220, process 200 can provide a human activity indication of the user based on the classification indication. In some examples, the human activity indication can be one or four human activity indications (e.g., an ambulation indication, a cycling indication, a sedentary indication, an others indication). In further examples, the ambulation indication for an adult can include walking: carrying load, stairs: inside and down, stairs: inside and up, treadmill: 3 mph 0% incline, treadmill: 3 mph 6% incline, treadmill: 3 mph 9% incline, treadmill: 2 mph 0% incline, treadmill: 4 mph 0% incline, natural walking, and the like. The ambulation indication for a youth can include natural walking, treadmill walking: 2 mph, treadmill walking: 3-4 mph, treadmill running: 4.5-5 mph, and the like. In further examples, the cycling indication for an adult or a youth can include: 70 rpm. 50 W, cycling outdoor level, cycling outdoor uphill, cycling outdoor downhill, and the like. In further examples, the sedentary indication for an adult or a youth can include: sitting with internet search, computer typing, writing, or reading, sorting files/paperwork, lying on back, left side, or right-side, sitting: legs straight, standing still, playing video game, and the like. In further examples, the others indication for an adult or a youth can include: painting, sweeping with broom, playing basketball, cleaning room, playing soccer, playing tennis, and the like. It should be appreciated that the categories and the activities are not limited to the list above. In addition, it should be appreciated that the classification indications can less than or more than four depending on the training of the deep learning model.

In some examples, process 200 can fine-tune or further train the trained machine learning model based on the spectrotemporal representation data for the user. In some examples, the trained deep learning model in step 216 may be a subject agnostic model. However, everyone's movement signature can be quite different where some people can be considered outliers compared to the general population. Then, the classification accuracies for these subjects typically drop statistically significantly below the average accuracy levels when using the subject agnostic model. However, by using a sub-transfer learning model (STLM), process 200 can boost the performance for these outlier subjects.

STLM is a powerful alternative to fine tune the accuracy of subject oriented classification problems in human activity recognition in healthcare. In STLM, similar principles of pre-training the model can be applied from transfer learning with the main difference in using the same dataset but with other users to boost the performance on new users with fine tuning unlike as in transfer learning where training is performed on a completely different domain dataset. In other words, a previously trained model can be reused with different subjects as the starting point for another model which can be trained/finetuned with only a handful of samples from the test subject and tested on the remaining majority samples of the test subject from the same dataset. The model which is trained using conventional training is repurposed on the test data to optimize the training performance and allow rapid updates to the fine-tuning process when modeling on the test subject of the same dataset. In order to achieve a fair comparison with subject-specific learning and enhance the classification accuracy, the minority oversampling method can be applied on the dataset to increase the number of test subject samples which are much fewer in number than the main dataset used in training the source model.

In other examples, as a baseline approach, subject-specific learning model (SSLM) can be used as a trivial technique where the training of the model starts from scratch, without transferring any knowledge from the pre-trained model. In this learning representation, the training is performed only on the training samples from the test subject and tested on the remaining samples. Since SSLM is trained and tested only on the test subjects individually, the size of the training data is augmented by generating the synthetic samples with artificial oversampling algorithm for a fair comparison with STLM and to boost the classification accuracy.

Figure 8:
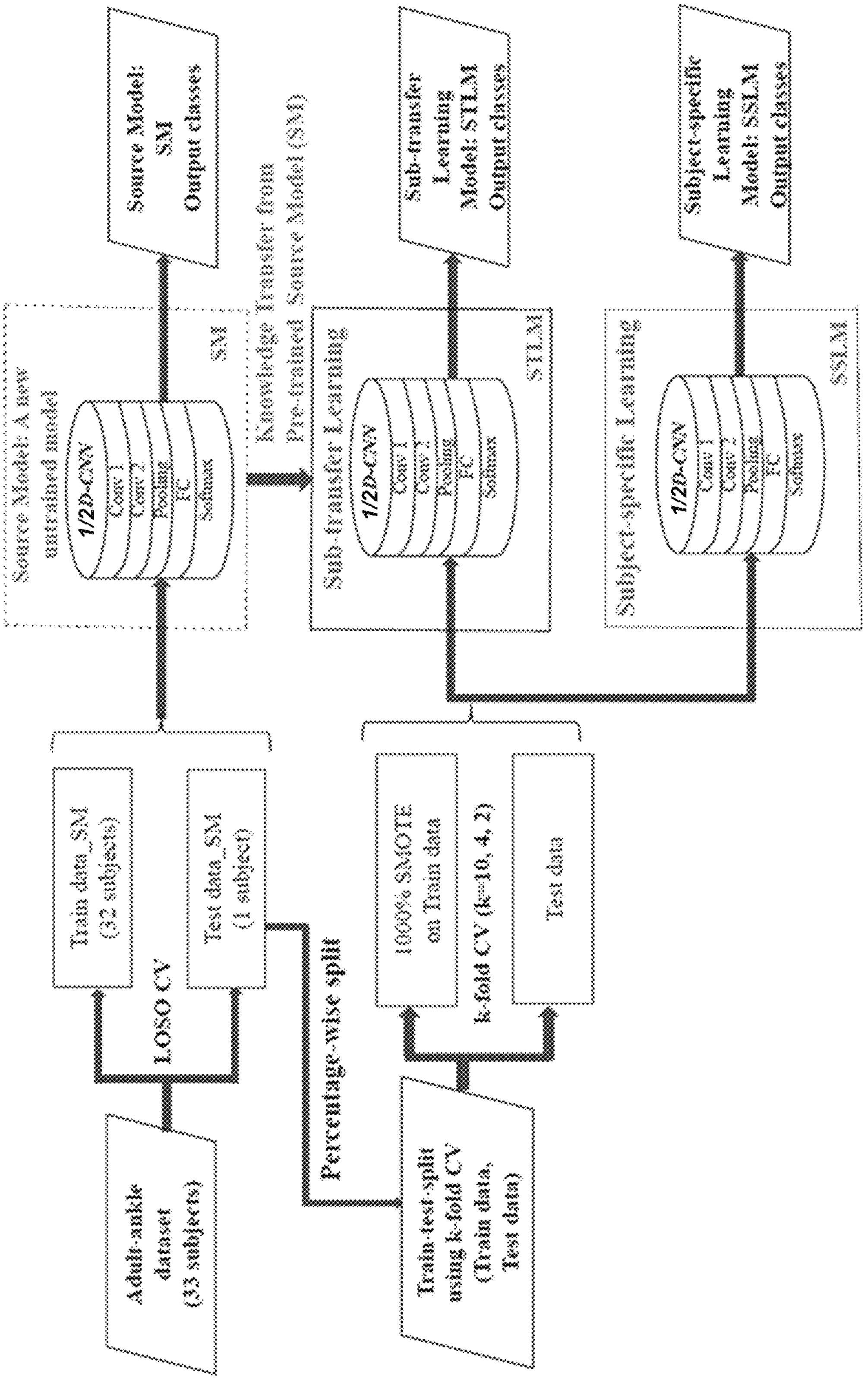
FIG. 8 illustrates an example block diagram of sub-transfer learning and subject-specific learning according to some embodiments.

Referring to FIG. 8, the framework of sub-transfer learning model along with the source on the sensor data (e.g., adult-ankle dataset with 33 subjects) and subject specific learning model. FIG. 8 displays the two learning representations with the 1D-CNN or 2D-CNN classifier. First, the train-test-split is performed on the adult-ankle dataset using 33-folds to implement leave-one-subject-out (LOSO) cross-validation to generate the train data SM from 32 subjects and the test data SM from the remaining subject. The training and validation of the models are then completed using the following steps:

A new untrained 1D-CNN or 2D-CNN model is trained on the 32 subject training data to create the large source model (SM) which is then tested on test data SM to record the subject-oriented classification accuracies.

Test data SM from the previous step is split into five combinations to train STLM and SSLM using 10, 4 and 2-fold cross validation to create the following training & testing split: 10%, 25%, 50%, 75% and 90% for training and the rest for testing respectively. As shown in FIG. 4, these splits are called train and test data.

To avoid the imbalanced classification problem and boost the performance of the classifier, some embodiments may augment the size of the training data by 11-folds by applying SMOTE on train data. Moreover, random oversampling can be used as a data augmentation technique for the cases where the number of samples from the minority class is ≤1. The N=11 parameter was chosen experimentally such that the augmented data is comparable in size to the data used to train the SM without too much repetition.

Then STLM, which includes a deep 1D-CNN classifier or a 2D-CNN classifier, is trained on train data using the knowledge (previous parameters) from the SM to classify the ADLs on test data.

To do a fair comparison, the same data (Train data, Test data) can be used as the input to the SSLM. In this example, the only difference between STLM and SSLM is that the SSLM is trained from scratch whereas STLM is trained by retuning of the SM parameters using the augmented data from the subject.

The operational algorithms for both SM and the subsequent STLM for 1D-CNN are shown in FIGS. 9 and 10, respectively. For example, in FIG. 9, the resampled and filtered sensor data is represented as $$\Omega_{in} = (X_{S_k}^{f_n}, Y_{S_k}), \text{ where } X_{S_k}^{f_n}$$

is an array of m dimensions, $$X_{S_k}^{f_n} = \{x_{S_k}^{f_0}, x_{S_k}^{f_1}, \ldots, x_{S_k}^{f_m}\}$$

and $S_k$ is the number of subjects for k=1, 2, . . . , l. For adult datasets, l=33 and for youth datasets, l=20. $Y_{S_k}$ represents the targets/labels or classes of the dataset. In line 1, an empty list 'Acc_list' is initialized. In line 2 to 18, 'for i←1 to l do' indicates a for loop which iterates over the range of numbers from 1 to l (for adult, l=33 subjects and for youth, l=20 subjects) and executes a sequence of operations mentioned inside the for loop. For each iteration in the for loop, firstly leave-one-subject-out (LOSO) cross validation (CV) is performed to generate Train data SM and Test data_SM. In each fold of LOSO CV, Test data_SM is generated using the observations of one subject and Train data_SM is generated using the observations of all remaining subjects. For $i^{th}$ subject, $$\text{Train\_x}[i] = \{x_{S_k}^{f_0}, x_{S_k}^{f_1}, \ldots, x_{S_k}^{f_m}\},$$

$$\forall k \neq i \text{ and Test\_x}[i] = \{x_{S_i}^{f_0}, x_{S_i}^{f_1}, \ldots, x_{S_i}^{f_m}\},$$

for k=i which are shown in line 4 and 5. The next two lines show that for the $i^{th}$ subject, Train data_SM[i] is formed by merging the array, Train_x[i] to its labels/classes. Similarly, the array of labels/classes of Test_x[i] is merged with it to form Test data_SM[i]. Secondly, from line 8 to 11, a nested for loop iterates over a certain range of numbers, 'num' to perform training of 1D-CNN model on Train data_SM[i]. During training of 1D-CNN, the error from the output of fully connected layer back-propagates to adjust the model parameters and the model computes the training accuracy. Line 12 to 16 describe that if the model converges, the trained model predicts the labels/classes on the Test data_SM[i] and computes the test accuracy which is then appended into the list 'Acc_list'. The steps from 1 to 16 are repeated in each of the l-folds CV or LOSO CV and test accuracies are saved in an empty list. Finally, the model is saved as a source model.

In FIG. 10, the $1^{st}$ states to repeat the steps of the source model for 1D-CNN and an empty list, 'accuracyList' is initialized in line 2. Since the algorithm considers only the Test data_SM to train and test the sub-transfer learning, the algorithm examines the different percentages of samples from the Test data SM to train a proposed STLM. In line 3 'train_size' is a list of different percentages of training samples. Line 4 to 39 represent a for loop by 'for i←1 to len(train_size) do' which iterates over a range of numbers starting from 1 to the length of the list of train_size which is 5. The loop iterates in such a way that for $1^{st}$ iteration, j=1 and tr_size=10%; for $2^{nd}$ iteration, j=2 and tr_size=25% and so on. For $1^{st}$ and $5^{th}$ iterations tr_size is 10% and 90% respectively which indicates a CV of 10 folds. For $2^{nd}$ and $4^{th}$ iterations tr_size is 25% and 75% respectively which indicate a CV of 4 folds and finally in the $3^{rd}$ iteration tr_size is 50% and CV is 2 folds. line 6 to 14 define three if-else loops which decide the number of cross validations of each set of tr_size data. Line 15 initializes an empty list. 'testx' and 'testy' represent the features and targets matrices of test data of $i^{th}$ subject which is 'Test data_SM[i]'. Line 18 to 35 show a nested for loop 'for tr_id, is_id in cross_val.split (testx,testy) do' which performs the cross validation split of the test dataset (testx and testy) by considering train and test indices (tr_id and is_id) to generate training and test data ('Train_data' and 'Test_data') and then augments the size of the 'Train data' using SMOTE. Then the parameters of the source model for 1D-CNN algorithm are uploaded (line 25). From line 26 to 29, another for loop inside the cross validation for loop indicates that the loop iterates over a range of numbers from 1 to a certain number 'num' to fine tune the source model by training on 'tr_sonte' and computing the training accuracy of the model. Line 30 to 33 show that if the model converges, then it predicts the test labels and compute the 'test_accuracy' which is then appended into a list, 'accList'. Line 36 converts the 'accList' to an array and then average accuracy of all folds is computed which is then appended to another list, accuracyList' in line 38 for each percentage of 'tr_size'.

The operational algorithms for both SM and the subsequent STLM for 2D-CNN are shown in FIGS. 11 and 12, respectively. In FIG. 11, unlike the algorithm in FIG. 9, the one-dimensional data is converted to two-dimensional spectrogram representation using 'Spect' function which is defined in line 1 to 15. In this 'Spect' function, the input data, $\omega_{in}$ is represented by its features $$(x_{S_k}^{f_n})$$

and targets ($y_{S_k}$) which is then randomly shuffled in line 3. Line 4 and 5 shows the features matrix and targets matrix respectively after a random shuffle. Line 6 initializes an empty list 'ab'. Line 7 to 13 define a for loop which iterates from j=1 to the length of the feature matrix and compute the spectrogram representation of features matrix using specific parameters such that kaiser window of (128, 18) size, overlapping samples=64, 64-point DFT and sampling rate=90 Hz. The spectrogram image for each observation of the dataset is displayed by (13, 13) dimension and absolute values of the (13,13) images are saved in a list, 'ab' and considered as the spectrogram data to train the model after converting the list to an array in line 14. So, this 'Spect' function returns the spectrogram data and its corresponding labels/classes. In line 16, when the 'Spect' function is called, it performs the sequence of operations to generate the spectrogram data from the given input data, $$(X_{S_k}^{f_n}, Y_{S_k}),$$

the function generates spectrogram features matrix ('spect') from $$X_{S_k}^{f_n}$$

and the corresponding labels ($dY_{S_k}$). From line 18 to 33 the steps follow the similar operations on spectrogram data ('spect') and its corresponding labels ($dY_{S_k}$), following the steps described in the lines 2 to 18 in SM for 1D-CNN.

FIG. 12 shows an example of pseudocode of an STLM model algorithm using a 2D-CNN algorithm. In algorithm 4, lines 1 to 24 follow the same steps which are mentioned in line 1 to 24 in algorithm 2 (FIG. 10). In line 25 and 26 'Spect' function is called on augmented train data ('tr_smote') and test data ('Test_data') respectively to generate the spectrogram representations of augmented training data and test data and their respective labels. In addition, line 28 to 42 follow the same procedure which is described in line 25 to 39 in algorithm 2 except training a 2D-CNN model instead.

In further examples, process 200 can receive an input for the human activity indication of the user. In some examples, the input can be a different human activity indication from the human activity indication resulted from the trained deep learning model. In response to the input, process 200 can further tune the trained deep learning model in a semi-supervised fashion. For example, the human activity indication based on the classification indication from the trained deep learning model is an ambulation indication. However, the actual activity of the user is cycling. Then, the user provides feedback indicating the human activity indication is cycling. Then, process 200 can consider the cycling indication as a ground truth label and tune or train the trained deep learning model.

Example Machine Learning Training Process

Figure 13:
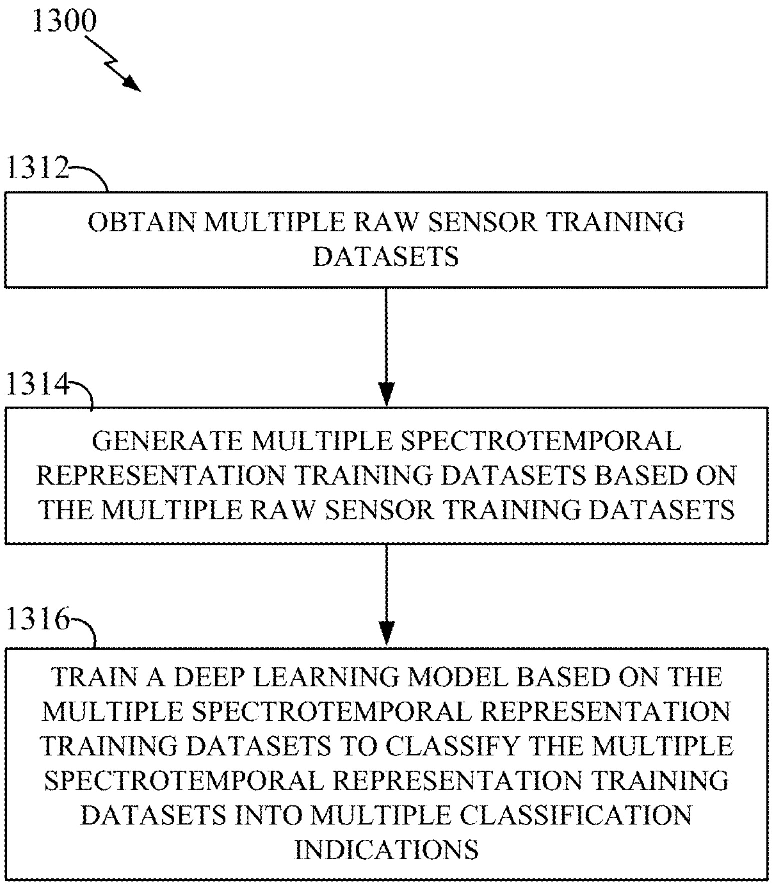
FIG. 13 is a flow diagram illustrating an example process for machine learning model training for human activity recognition according to some embodiments.
Figure 14:
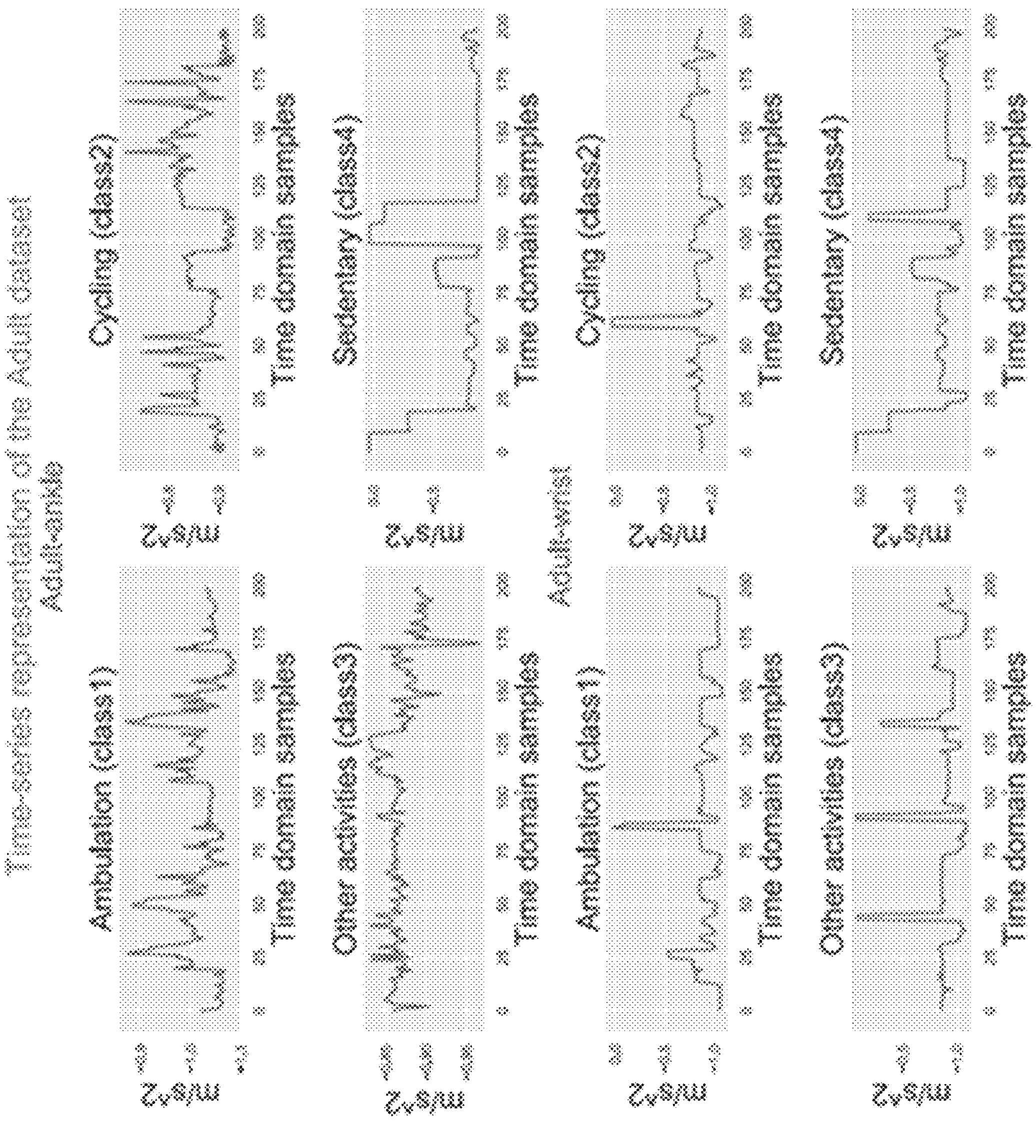
FIG. 14 illustrates an example time-series sensor data of single-axis acceleration data for four classes of activities of daily living for the adult-ankle and adult-wrist datasets according to some embodiments.

FIG. 13 is a flow diagram illustrating an example process 1300 for machine learning model training for human activity recognition in accordance with some aspects of the present disclosure. As described below, a particular implementation can omit some or all illustrated features/steps, may be implemented in some embodiments in a different order, and may not require some illustrated features to implement all embodiments. In some examples, an apparatus (e.g., computing device 110, processor 112 with memory 114, etc.) in connection with FIG. 1 can be used to perform example process 1300. However, it should be appreciated that any suitable apparatus or means for carrying out the operations or features described below may perform process 1300.

At step 1312, process 1300 can obtain multiple raw sensor training datasets. In some examples, the multiple raw sensor training datasets is substantially similar to the sensor data at step 212 of FIG. 2. The difference is that the multiple raw sensor training datasets are classified different groups for training purposes. For example, the inventors used datasets of different ages, genders and sensor-locations for a research group at Stanford. The overall data collection process included 53 participants with 33 adults and 20 youths. The suits of synchronized sensors were placed on ankles and wrists of the participants who were directed to perform a sequence of common physical activities, lasting 3-5 minutes each. In this data collection process, triaxial accelerometers, which are small and lightweight devices, were placed on the wrist and ankle positions of the participants using custom bands (e.g., Velcro® bands). Based on the ages of the participants and the locations of the sensors on the body, the datasets are classified into four distinct groups: (1) adult-ankle, (2) adult-wrist, (3) youth-ankle and (4) youth-wrist as shown in FIG. 12. FIG. 12 illustrates an example time-series sensor data of single-axis acceleration data for four classes of activities of daily living for the adult-ankle and adult-wrist datasets. Table 1 provides the sample sizes of four different datasets. Twenty-five experiments were included on four datasets when considering six classification algorithms for each dataset.

TABLE 1

Number of observations of four Adult-Youth datasets

| Dataset | Observations |
|---|---|
| Adult-ankle | 12812 |
| Adult-wrist | 12618 |
| Youth-ankle | 7910 |
| Youth-wrist | 7869 |

These common daily activities are shown in Table 2 and can be categorized into four main classes: ambulation, cycling, other activities and sedentary.

TABLE 2

Activities of daily living categorized into four classes

| Class | Activities of Adult Dataset | Activities of Youth Dataset |
|---|---|---|
| Ambulation | Walking: carrying load | Walking, natural |
| | Stairs: inside and down | Treadmill walking: 2 |
| | Stairs: inside and up | Treadmill walking: 3-4 mph |
| | Treadmill: 3 mph 0% incline | Treadmill running: 4.5-5 mph |
| | Treadmill: 3 mph 6% incline | — |
| | Treadmill: 3 mph 9% incline | — |
| | Treadmill: 2 mph 0% incline | — |
| | Treadmill: 4 mph 0% incline | — |
| | Walking, natural | — |
| Cycling | 70 rpm. 50 W. 0.7 kg | 70 rpm 50 watts |
| | Cycling outdoor level | Outdoor cycling |
| | Cycling outdoor uphill | — |
| | Cycling outdoor downhill | — |
| Others | Painting: roller | Basketball: -dribbling |
| | Painting: brush | Basketball: -passing |
| | Sweeping with broom | Basketball: -shortshots |
| | — | Clean room |
| | — | Soccer: -dribbling |
| | — | Soccer: -passing |
| | — | Tennis-ball: -fielding |
| | — | Tennis-ball: -throwing-catching |
| Sedentary | Sitting, internet search | Sitting: reading |
| | Sitting, computer typing | Play-computer-game |
| | Sitting: writing | Play-on-gameboy |
| | Sitting: reading | Wii: -boxing |
| | Sorting files/paperwork | Wii: -tennis |

TABLE 2-continued

| Activities of daily living categorized into four classes | | |
|---|---|---|
| Class | Activities of Adult Dataset | Activities of Youth Dataset |
| | Lying: on back | Lying: on back |
| | Lying on left side | Sitting: legs straight |
| | Lying on-right-side | Standing still |
| | Sitting: legs straight | — |
| | Standing still | — |

At step 1314, process 1300 can generate multiple spectrotemporal representation training datasets based on the multiple raw sensor training datasets. In some examples, this step to generate multiple spectrotemporal representation training datasets is substantially similar to the generation step 214 of FIG. 2. While the sensor data corresponds to the spectrotemporal representation data in step 214 of FIG. 2, multiple spectrotemporal representation training datasets can correspond to or more than the multiple raw sensor training datasets because some datasets in a minority class can be augmented with synthetic spectrotemporal datasets.

In some examples, process 1300 augment the number of observations using the Synthetic Minority Over Sampling Technique (SMOTE) specifically for the youth-ankle dataset where the performance lagged behind subject agnostic features. Process 1300 can further generate synthetic spectrotemporal datasets directed to a first classification indication of the multiple classification indications. In some examples, a first amount of datasets in the first classification indication can be smaller than a second amount of datasets in another classification indication of the multiple classification indications. In some examples, the synthetic spectrotemporal datasets are included in the multiple spectrotemporal representation training datasets. A first synthetic spectrotemporal dataset of the synthetic spectrotemporal datasets is generated with interpolation between two non-synthetic spectrotemporal datasets in the multiple spectrotemporal representation training datasets. In some examples, two non-synthetic spectrotemporal datasets are in the first classification indication.

Figure 15:
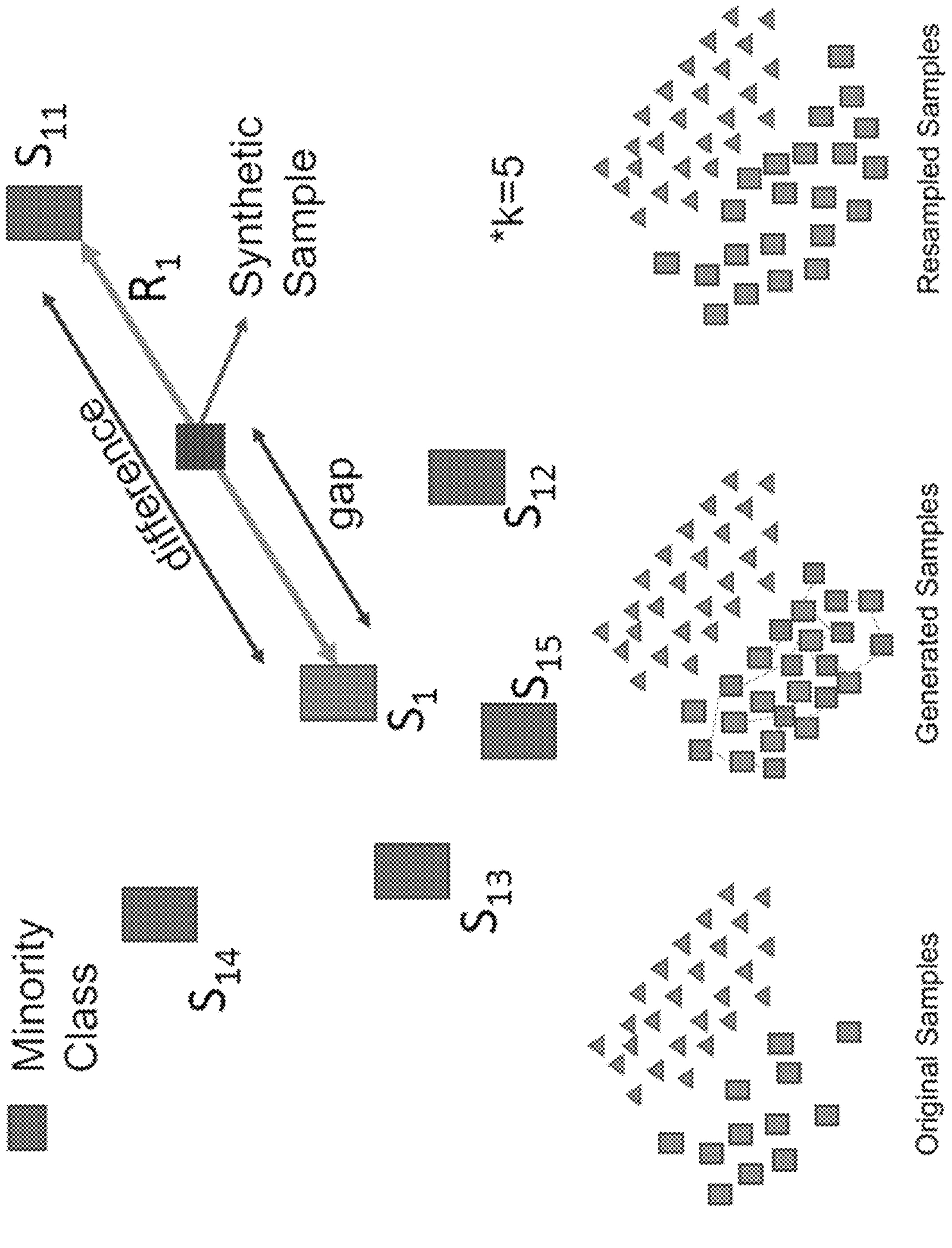
FIG. 15 illustrates an example process to generating synthetic samples using a synthetic minority over sampling technique (SMOTE) according to some embodiments.

Overall, the 2D-CNN provides better classification accuracies in the raw data-space than the feature space. On the contrary, the feature learner does not perform as well on the youth-ankle dataset. This could be due to a number of reasons including the entropy of the dataset and the number of observations available to train the large number of trainable parameters. In these instances, synthetic data augmentation techniques such as SMOTE can substantially improve performance as evident from modern image classification applications. SMOTE oversamples the minority class by taking each class sample and generating synthetic samples along the line segments joining its k nearest neighbors. Depending upon the desired level of over-sampling, neighbors are randomly selected from the k nearest neighbors as follows: $S'=S+rand(0,1)*|S-S_k|$, where S' denotes the new set of synthetic samples, S is the set of original samples for which k-nearest neighbors are being identified and $S_k$ is the set of randomly selected k-nearest neighbor samples. To generate new samples, this process is repeated N number of times where N is the oversampling rate commonly provided as a percentage. In some examples, in four different levels of oversampling, diminishing returns are demonstrated as the synthetic samples begin to contribute less and less meaningful information to the training process. FIG. 15 shows the basic operational principle of SMOTE graphically as new samples are generated between the original samples $S_1$ and $S_{11}$ for instance.

At step 1316, process 1300 can train a deep learning model based on the multiple spectrotemporal representation training datasets to classify the multiple spectrotemporal representation training datasets into multiple classification indications. In some examples, the deep learning model is trained using leave-one-subject-out cross-validation with a random shuffle. In further examples, the deep learning model is an unsupervised deep learning model. The deep learning model is a one-dimensional or two-dimensional convolutional neural network model.

The inventors tested a wide array of topologies using grid hyperparameter search, and the best topology has been chosen for each classifier to train the raw data using leave-one-subject-out (LOSO) cross-validation with a random 'shuffle' to estimate an unbiased and accurate model performance for all experiments. For two adult datasets, inventors considered LOSO with k-fold=33 and for the remaining two youth datasets, k-fold=20 is used to implement cross-validation during the training process. Table 3 summarizes the best topologies used to train the 1D-CNN and 2D-CNN classifiers and shows the number of hidden neurons (HNs) for each hidden layer (HL) such as HL1, HL2 etc.

TABLE 3

| The topologies for the different classifiers using feature learning for human activity recognition | | | | |
|---|---|---|---|---|
| Classifier | HNs (HL1) | HNs (HL2) | HNs (HL3) | HNs (HL4) |
| 1D-CNN | 250 | 250 | 50 | 20 |
| 2D-CNN | 500 | — | — | — |

Example Data

In order to conduct a fair comparison with the original paper from the Stanford group, the inventors applied the same LOSO cross-validation as the inventors trained & tested six different classification algorithms on raw data and features separately for adult and youth datasets where the feature engineering is represented by the prior results. Moreover, the inventors performed the classification experiments on these four datasets using other and more recent state-of-the-art features to provide a robust comparison between deep learning and feature engineering. For deep feed-forward neural network (DFNN), 1D-CNN, 2D-CNN and recurrent neural network with long short-term memory (RNN-LSTM), the resampled and filtered data is represented at the input layer as-is. The autoencoder deep feed-forward neural network (AE-DFNN) on the other hand is first trained to learn the unsupervised features from the latent space of raw data where the extracted latent features are subsequently used to train another dense FNN.

TABLE 4

| Average accuracies for the different classifiers using feature learning versus the subject agnostic feature engineering used in the latest work on this dataset | | | | |
|---|---|---|---|---|
| | Average classification accuracy (%) | | | |
| Classifier | Adult-ankle | Adult-wrist | Youth-ankle | Youth-wrist |
| DENN | 91.17 ± 3.47 | 87.43 ± 7.87 | 85.86 ± 10.43 | 88.30 ± 8.3 |
| AE-DFNN | 88.33 ± 4.81 | 81.31 ± 7.74 | 82.68 ± 10.78 | 80.81 ± 8.04 |

TABLE 4-continued

| Average accuracies for the different classifiers using feature learning versus the subject agnostic feature engineering used in the latest work on this dataset | | | | |
|---|---|---|---|---|
| | Average classification accuracy (%) | | | |
| Classifier | Adult-ankle | Adult-wrist | Youth-ankle | Youth-wrist |
| 1D-CNN | 95.21 ± 2.38 | 88.02 ± 6.29 | 88.49 ± 8.98 | 90.54 ± 4.98 |
| 2D-CNN | 95.57 ± 2.54 | 93.45 ± 3.55 | 93.38 ± 2.67 | 93.13 ± 3.5 |
| Existing Model | 94.8 | 87 | 92.4 | 91 |
| FE-DFNN | 92 ± 4.38 | 83.78 ± 8.45 | 85.79 ± 9.82 | 85.86 ± 8.47 |

Figure 16:
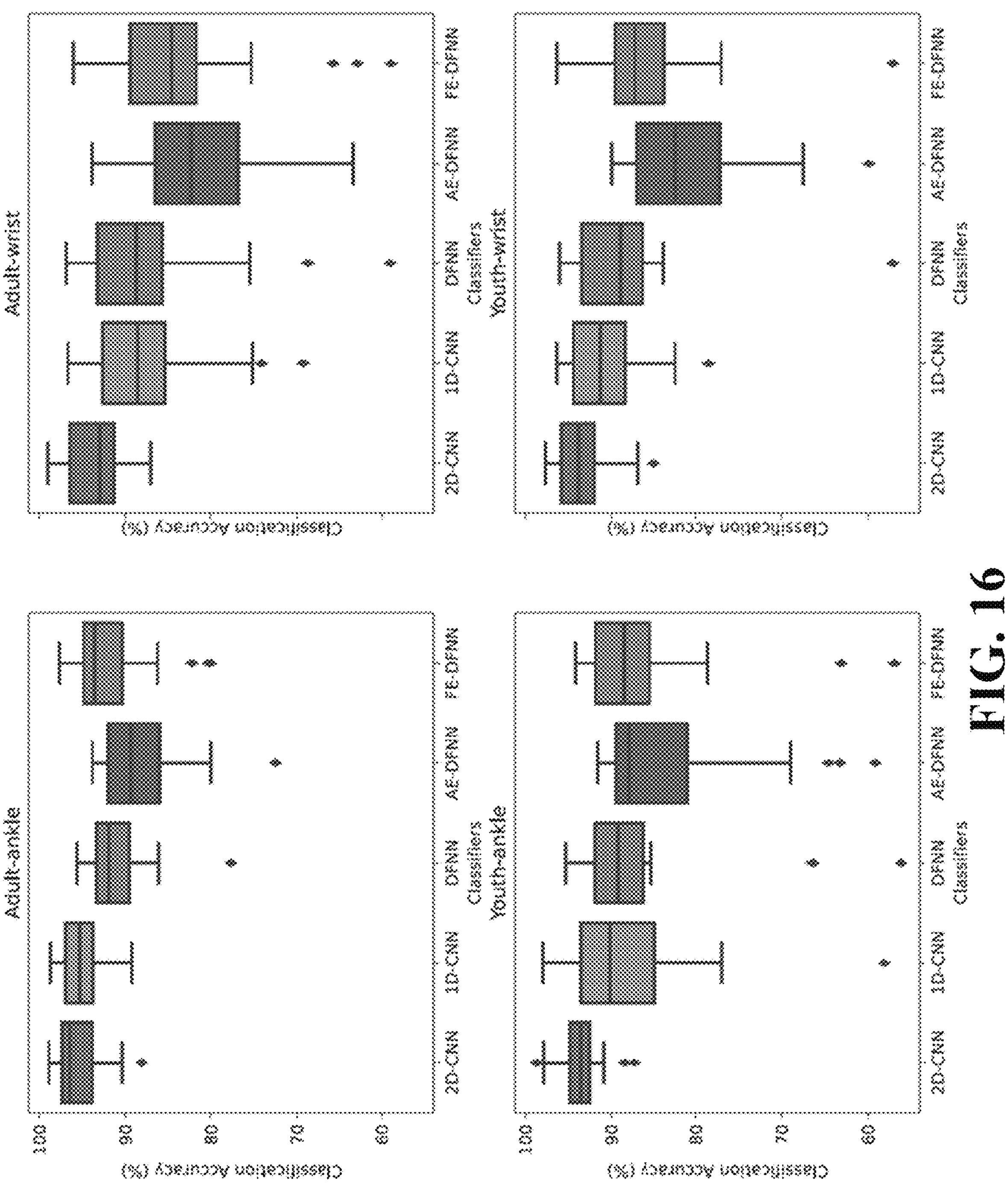
FIG. 16 illustrates boxplot distributions of classification accuracies across different classifiers according to some embodiments.

Table 4 represents the average classification accuracies with standard deviations across the four datasets for all models with LOSO cross-validation. The inventors observed that even though the best result in each dataset is observed for the 2D-CNN feature learning deep neural network, the significance of proper learning representation is highlighted by the fact that human engineered features can actually outperform deep learning when the topology is not carefully selected (i.e., both for regular feedforward neural network and for the autoencoder feature learner). Ultimately, results indicate state-of-the-art performance using a 2D-CNN model on raw data which outperformed the most recent results reported on the dataset using feature-based models. The table also provides a one-to-one comparison of the best accuracies reported in this paper with the most recent results on this dataset as well as the performances of FE-DFNN models using more recent state-of-the-art features for motion data (not particularly tuned for this dataset). Inventor's findings from these experiments reveal that the subject agnostic features perform much better compared to the FE-DFNN classifier. However, the performances of convolutional feature learners, especially with spectrotemporal features, outperform the feature engineering classifiers. FIG. 16 shows the boxplots for the accuracies of five classification algorithms including FE on four datasets for a better statistical comparison. These results are all statistically significantly relevant as discussed further in the next subsection.

Figure 17:
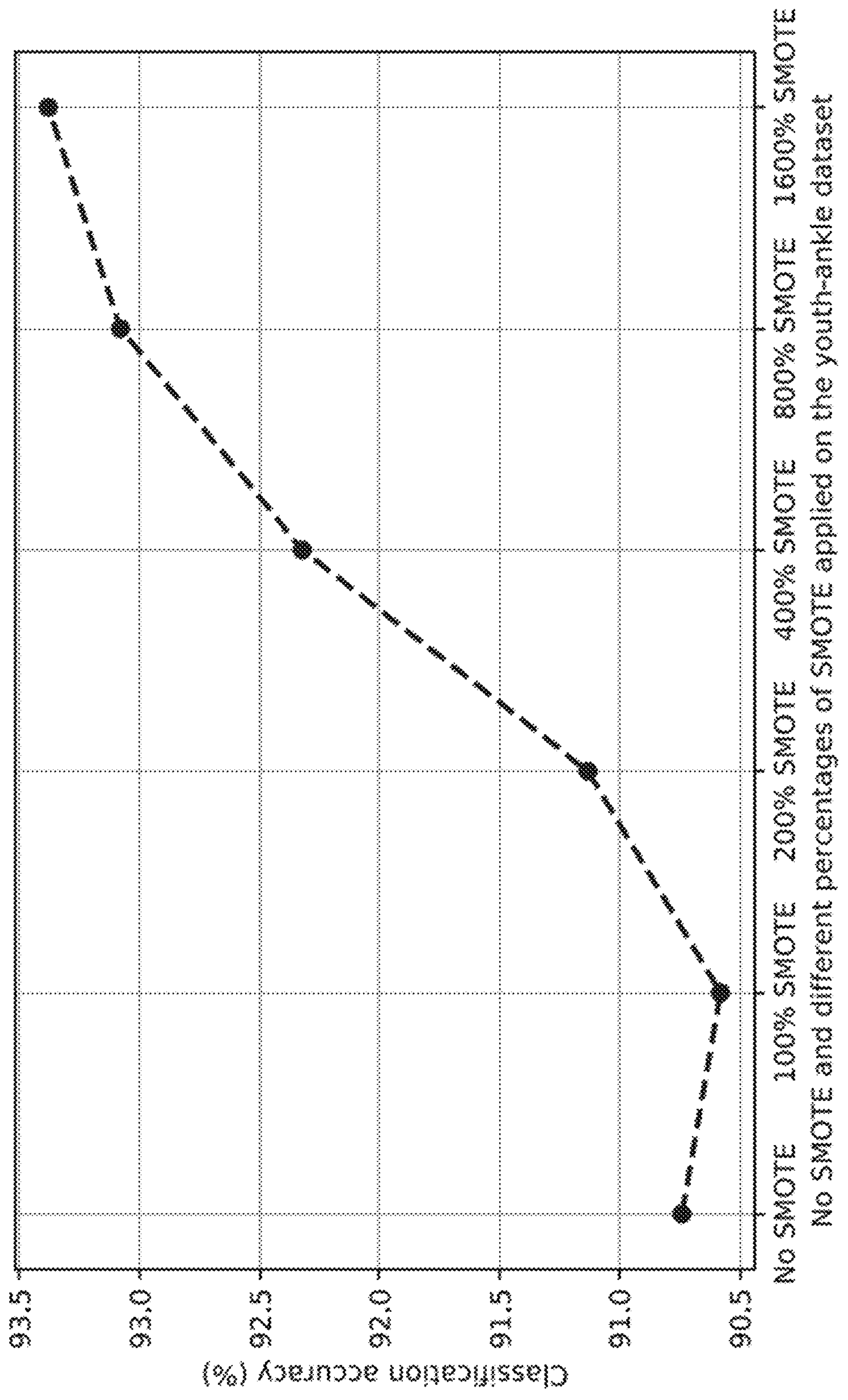
FIG. 17 illustrates average classification accuracies of 2D-CNN classifier with no SMOTE and different percentages of SMOTE on sensor data according to some embodiments.

Another observation was the requirement to support the training of the more complex 2D-CNN algorithm via a synthetic data augmentation method called SMOTE at different levels of oversampling. Table 5 displays the average classification accuracies with standard deviations of the 2D-CNN classifier on the youth-ankle dataset with and without data augmentation. As one can see, without any augmentation, the accuracy of the 2D-CNN classifier is actually slightly worse than the subject agnostic features, 90.74% versus 92.4%. It is only through augmentation that the 2D-CNN model manages to outperform the current state-of-the-art reported in the literature. FIG. 17 clearly shows the significant increases in performance as more synthetic samples are included in the training process. The diminishing returns are also apparent as when more samples are included in the training process, the classification accuracy no longer displays the same level of improvement.

TABLE 5

| Average classification accuracies with and without data augmentation on the youth-ankle dataset<br>Average classification accuracy (%) | | | | | |
|---|---|---|---|---|---|
| Without SMOTE | 100% SMOTE | 200% SMOTE | 400% SMOTE | 800% SMOTE | 1600% SMOTE |
| 90.74 ± 3.57 | 90.58 ± 3.26 | 91.13 ± 3.1 | 92.32 ± 2.3 | 93.08 ± 2.51 | 93.38 ± 2.67 |

In a recently published article, the highest accuracies on domain-specific features reported for adult-ankle, adult-wrist, youth-ankle and youth-wrist datasets are 94.8%, 87%, 92.4% and 91% respectively using domain specific features with a support vector machine classifier. The highest classification accuracies in this disclosure are achieved using 2D-CNNs on raw temporal data on the same datasets with 95.57%, 93.57%, 93.38% and 93.13% respectively. These results suggest that raw data can compete and often outperform FE and that the latent features extracted by a 2D-CNN on rich spectrogram images perform better than both the human engineered features and the fully unsupervised feature learning using an autoencoder. This research demonstrated the competitiveness of feature learning especially when coupled with data rich input representations such as spectrograms which can be obtained from temporal activity recognition signals.

TABLE 6

| Statistical significance analysis between the performances of the classifiers on Adult dataset | | |
|---|---|---|
| Classification Algorithms | Null Hypothesis (h) | p-value (p) |
| Adult-ankle Dataset | | |
| 2D-CNN vs. 1D-CNN | 0 | 0.272 |
| 2D-CNN vs. DFNN | 1 | 3.54E−06 |
| 2D-CNN vs. AE-DFNN | 1 | 7.11E−07 |
| 2D-CNN vs. FE-DFNN | 1 | 3.53E−05 |
| 1D-CNN vs. DFNN | 1 | 5.39E−07 |
| 1D-CNN vs. AE-DFNN | 1 | 5.91E−07 |
| 1D-CNN vs. FE-DFNN | 1 | 4.99E−06 |
| DFNN vs. AE-DFNN | 1 | 0.001 |
| DFNN vs. FE-DFNN | 1 | 0.009 |
| AE-DFNN vs. FE-DFNN | 1 | 9.45E−05 |
| Adult-wrist Dataset | | |
| 2D-CNN vs. 1D-CNN | 1 | 2.98E−06 |
| 2D-CNN vs. DFNN | 1 | 4.58E−06 |
| 2D-CNN vs. AE-DFNN | 1 | 1.02E−06 |
| 2D-CNN vs. FE-DFNN | 1 | 5.39E−07 |
| 1D-CNN vs. DFNN | 0 | 0.598 |
| 1D-CNN vs. AE-DFNN | 1 | 4.45E−05 |
| 1D-CNN vs. FE-DFNN | 1 | 1.69E−04 |
| DFNN vs. AE-DFNN | 1 | 0.0001 |
| DFNN vs. FE-DFNN | 1 | 1.47E−05 |
| AE-DFNN vs. FE-DFNN | 1 | 0.023 |

TABLE 7

| Statistical significance analysis between the performances of the classifiers on Youth dataset | | |
|---|---|---|
| Classification Algorithms | Null Hypothesis (h) | p-value (p) |
| Youth-ankle Dataset | | |
| 2D-CNN vs. 1D-CNN | 1 | 0.001 |
| 2D-CNN vs. DFNN | 1 | 0.0001 |
| 2D-CNN vs. AE-DFNN | 1 | 8.86E−05 |

TABLE 7-continued

Statistical significance analysis between the performances of the classifiers on Youth dataset

| Classification Algorithms | Null Hypothesis (h) | p-value (p) |
|---|---|---|
| 2D-CNN vs. FE-DFNN | 1 | 2.54E−04 |
| 1D-CNN vs. DFNN | 0 | 0.03 |
| 1D-CNN vs. AE-DFNN | 1 | 0.001 |
| 1D-CNN vs. FE-DFNN | 0 | 0.145 |
| DFNN vs. AE-DFNN | 0 | 0.025 |
| DFNN vs. FE-DFNN | 0 | 0.737 |
| AE-DFNN vs. FE-DFNN | 0 | 0.247 |
| Youth-wrist Dataset | | |
| 2D-CNN vs. 1D-CNN | 1 | 0.01 |
| 2D-CNN vs. DFNN | 1 | 0.0003 |
| 2D-CNN vs. AE-DFNN | 1 | 8.86E−05 |
| 2D-CNN vs. FE-DFNN | 1 | 2.19E−04 |
| 1D-CNN vs. DFNN | 0 | 0.021 |
| 1D-CNN vs. AE-DFNN | 1 | 8.86E−05 |
| 1D-CNN vs. FE-DFNN | 1 | 2.54E−04 |
| DFNN vs. AE-DFNN | 1 | 0.0002 |
| DFNN vs. FE-DFNN | 1 | 0.03 |
| AE-DFNN vs. FE-DFNN | 1 | 5.93E−04 |

To compare the statistical significance of the classification results, the inventors performed a statistical significance test between each pair of classifiers. Since the outcomes of the goodness of fit test and the variance test using subject based classification accuracies of deep learning classifiers do not follow the conventional assumptions on the data distribution (such as Gaussian (normal) distribution) and the data samples cannot necessarily be assumed as independent, the inventors followed a non-parametric approach for statistical testing. More specifically, as the subject-based classification accuracies of two classifiers come from the same population and the data is paired, the inventors performed a non-parametric Wilcoxon signed-rank test, a popular statistical test for paired data which does not come from a normal distribution, to investigate the null hypothesis. The data distributions of all the proposed models (with or without feature engineering) are dependent as the features are still drawn from the raw data of the same subjects. Hence, the inventors employed the same Wilcoxon signed-rank test for hypothesis test between the deep learning models versus the feature-based model. Tables 6 and 7 show that the feature engineering model (FE-DFNN) performs statistically significantly worse than the raw models where the null hypothesis is rejected (h=1) for every dual comparison on three out of four datasets except on the youth-ankle dataset, where all algorithms have statistically the same performance except for 2D-CNN which is statistically significantly better than all the other models. Furthermore, the 2D-CNN model which utilizes spectrotemporal features automatically learned from the raw data, statistically significantly outperforms every other model in every single scenario except one. On the adult-ankle dataset, both convolutional models display the same performance, though still significantly better than the competing approaches. However, for this specific case, it is still important to note that even a small performance difference (in this case 0.36%) when properly cross-validated across the subject-specific dataset still holds value for the machine learning community at large. Finally, the inventors found that the test fails to reject the null hypothesis (h=0) for 1D-CNN vs. DFNN on adult-wrist, youth-ankle and youth-wrist datasets which further demonstrated that spectral properties of the signal should be taken into account for classification purposes.

TABLE 8

Computational complexities of five classifiers for a single subject on four datasets

| Classifier | Accuracy (%) | Epochs | Training Time (S) | Test Time (S) | Computational Time (S) | Computational Time/epoch (S) | Training Parameters |
|---|---|---|---|---|---|---|---|
| Adult-ankle Dataset, Subject-14 | | | | | | | |
| DFNN | 95.15 | 200 | 159 | 0.11 | 159.11 | 0.8 | 750754 |
| AE-DFNN | 90.61 | 1700 | 1528.95 | 1.607 | 1530.56 | 0.9 | 2796617 |
| 1D-CNN | 97.58 | 1000 | 15589.27 | 0.25 | 15589.53 | 15.59 | 7257646 |
| 2D-CNN | 98.49 | 500 | 368.2 | 0.18 | 368.38 | 0.74 | 1674632 |
| RNN-LSTM | 99.7 | 100 | 246182.98 | 13.77 | 246196.74 | 2461.97 | 815404 |
| Adult-wrist Dataset, Subject-7 | | | | | | | |
| DFNN | 82.25 | 1500 | 1132.2 | 0.11 | 1132.32 | 0.76 | 750754 |
| AE-DFNN | 53.84 | 1700 | 1018.30 | 1.55 | 1019.85 | 0.6 | 2796617 |
| 1D-CNN | 82.61 | 1000 | 15099.22 | 0.24 | 15099.46 | 15.1 | 7257646 |
| 2D-CNN | 85.87 | 800 | 577.52 | 0.204 | 577.72 | 0.72 | 1674632 |
| RNN-LSTM | 64.86 | 150 | 386677.11 | 10.42 | 386687.54 | 2577.92 | 815404 |
| Youth-ankle Dataset, Subject-3 | | | | | | | |
| DFNN | 85.08 | 1200 | 575.75 | 0.11 | 575.86 | 0.48 | 750754 |
| AE-DFNN | 76.82 | 1700 | 637.42 | 0.86 | 638.28 | 0.38 | 2796617 |
| 1D-CNN | 81.5 | 1000 | 9566.86 | 0.25 | 9567.12 | 9.57 | 7257646 |
| 2D-CNN | 87.16 | 800 | 371.64 | 0.21 | 371.84 | 0.47 | 1674632 |
| RNN-LSTM | 92.24 | 100 | 156094.16 | 13.43 | 156107.59 | 1561.08 | 815404 |
| Youth-wrist Dataset, Subject-4 | | | | | | | |
| DFNN | 93.4 | 1500 | 699.62 | 0.1 | 699.72 | 0.47 | 750754 |
| AE-DFNN | 78.72 | 1700 | 623.009 | 0.859 | 623.868 | 0.367 | 2796617 |
| 1D-CNN | 90.81 | 1500 | 14197.6 | 0.13 | 14197.73 | 9.47 | 7257646 |
| 2D-CNN | 94.25 | 630 | 280.7 | 0.21 | 280.91 | 0.45 | 1674632 |
| RNN-LSTM | 89.99 | 100 | 137337.16 | 11.17 | 137348.33 | 1373.48 | 815404 |

Table 8 shows the computational complexities and computational run times of the five classifiers. The computer used in this study is configured with the following specifications: Intel® Core™ i7 4.20 GHz CPU, NVIDIA GeForce GTX 1080 GPU and 32 gigabyte memory (RAM). From the table, the feature learning algorithms (AE-DFNN and 2D-CNN) display fast convergence in training. However, comparing the high classification rates and the low computational time for testing among all the classifiers, 2D-CNN provides the highest performance with the lowest computational times. The classification rate of an RNN-LSTM classifier for this dataset is investigated as well, for comparison purposes. Table 9 displays the RNN-LSTM classification-accuracies including computational time for three subjects randomly selected from each dataset and a comparison between the classification accuracies of 2D-CNN and RNN-LSTM algorithms for those subjects.

TABLE 9

Classification accuracies and computational time of RNN-LSTM classifier based on three random subjects of four datasets

| Subject | 2D-CNN Accuracy (%) | RNN Accuracy (%) | Epochs | Training Time (S) | Test Time (S) | Computational Time (S) |
|---|---|---|---|---|---|---|
| Adult-ankle Dataset | | | | | | |
| 1 | 95.52 | 92.41 | 53 | 123101.61 | 13.88 | 123115.49 |
| 3 | 92.86 | 90 | 50 | 123071.49 | 12.98 | 123084.47 |
| 14 | 98.86 | 99.7 | 100 | 246182.98 | 13.77 | 246196.74 |
| Adult-wrist Dataset | | | | | | |
| 1 | 93.96 | 93.46 | 100 | 259166.59 | 12.77 | 259179.36 |
| 7 | 89.86 | 82.68 | 135 | 348009.39 | 10.42 | 348019.81 |
| 10 | 98.54 | 93.21 | 100 | 289893.70 | 13.64 | 289907.34 |
| Youth-ankle Dataset | | | | | | |
| 1 | 92.76 | 88.69 | 100 | 150019.68 | 12.1 | 156106.26 |
| 2 | 94.41 | 93.01 | 100 | 158000.1 | 13.87 | 179271.62 |
| 3 | 91.54 | 92.24 | 100 | 156094.16 | 13.43 | 156107.59 |

TABLE 9-continued

Classification accuracies and computational time of RNN-LSTM classifier based on three random subjects of four datasets

| Subject | 2D-CNN Accuracy (%) | RNN Accuracy (%) | Epochs | Training Time (S) | Test Time (S) | Computational Time (S) |
|---|---|---|---|---|---|---|
| Youth-wrist Dataset | | | | | | |
| 1 | 84.91 | 84.71 | 150 | 214672.83 | 11.467 | 214684.3 |
| 3 | 91.05 | 66.57 | 100 | 137337.16 | 11.17 | 137348.33 |
| 7 | 97.68 | 95.07 | 150 | 216252.6 | 13.11 | 216265.71 |

In Table 9, the most interesting observation is that RNN-LSTM has significantly higher training time because of its recurrent feedback loop and for this reason the classification using this algorithm for LOSO cross-validation on this dataset is computationally expensive where it takes approximately 2-days to complete training only for a single subject partition out of the 53 subjects in the adult and youth datasets. More importantly however, it does not provide a better classification rate compared to 2D-CNN, so it was not considered for the full experimental analysis in this study.

Example Sub-Transfer Learning Data

The experimental setup described in the previous section is applied to three different subjects from each dataset with the training of a new untrained classification source model. The subjects are specifically chosen at the different outlier levels in the classification space (i.e., the highest, the median, and the lowest accuracies) to explore the performance of sub-transfer and subject-specific learning for a range of challenging tasks. Table 10 shows a robust comparison of the classification performances of STLM (where the knowledge from the previously trained model is transferred during additional training on some samples from the test dataset) and SSLM (where the model performs training only on the samples from the test subject without doing a previous training) on twelve subjects (three for each of the four datasets) and finally SM without any additional training using LOSO CV

TABLE 10

Experimental results of sub-transfer and subject-specific learning models

| Training data (%) | STLM ACC ± STD (%) | SSLM ACC ± STD (%) | SM ACC ± STD (%) | STLM ACC ± STD (%) | SSLM ACC ± STD (%) | SM ACC ± STD (%) | STLM ACC ± STD (%) | SSLM ACC ± STD (%) | SM ACC ± STD (%) |
|---|---|---|---|---|---|---|---|---|---|
| | Adult-ankle Dataset | | | | | | | | |
| | Subject-28 (Minimum) | | | Subject-31 (Maximum) | | | Subject-27 (Median) | | |
| 10 | 95.65 ± 1.08 | 71.65 ± 9.78 | 88.41 | 99.03 ± 0.74 | 73.56 ± 9.25 | 98.71 | 96.75 ± 1.73 | 71.50 ± 11.22 | 95.65 |
| 25 | 96.62 ± 1.08 | 88.11 ± 4.06 | | 98.92 ± 0.83 | 86.08 ± 4.72 | | 96.78 ± 2.14 | 87.38 ± 5.11 | |
| 50 | 96.82 ± 2.01 | 88.96 ± 3.42 | | 99.04 ± 0.45 | 96.14 ± 0.89 | | 97.22 ± 3.93 | 90.69 ± 2.55 | |
| 75 | 98.28 ± 2.20 | 91.93 ± 3.83 | | 99.68 ± 0.63 | 95.52 ± 2.16 | | 99.08 ± 1.17 | 94.45 ± 3.83 | |
| 90 | 98.29 ± 2.39 | 95.10 ± 3.60 | | 99.70 ± 0.96 | 98.35 ± 2.34 | | 1 ± 0.0 | 92.18 ± 6.34 | |
| | Adult-wrist Dataset | | | | | | | | |
| | Subject-6 (Minimum) | | | Subject-31 (Maximum) | | | Subject-33 (Median) | | |
| 10 | 79.35 ± 10.85 | 68.47 ± 7.03 | 66.15 | 96.06 ± 1.43 | 78.63 ± 3.84 | 96.03 | 97.92 ± 1.77 | 70.55 ± 5.85 | 90.82 |
| 25 | 87.50 ± 8.65 | 73.15 ± 6.11 | | 96.13 ± 1.17 | 86.32 ± 2.18 | | 98.08 ± 2.22 | 92.25 ± 2.77 | |
| 50 | 93.02 ± 9.87 | 78.20 ± 4.52 | | 96.70 ± 1.84 | 91.40 ± 1.79 | | 99.02 ± 1.39 | 89.86 ± 11.54 | |
| 75 | 96.97 ± 6.07 | 80.22 ± 4.13 | | 97.04 ± 2.44 | 92.41 ± 5.63 | | 99.35 ± 1.30 | 95.13 ± 5.01 | |
| 90 | 97.78 ± 5.84 | 85.97 ± 3.75 | | 99.38 ± 1.32 | 93.79 ± 3.84 | | 1 ± 0.0 | 98.98 ± 2.71 | |

TABLE 10-continued

Experimental results of sub-transfer and subject-specific learning models

| Training data (%) | STLM ACC ± STD (%) | SSLM ACC ± STD (%) | SM ACC ± STD (%) | STLM ACC ± STD (%) | SSLM ACC ± STD (%) | SM ACC ± STD (%) | STLM ACC ± STD (%) | SSLM ACC ± STD (%) | SM ACC ± STD (%) |
|---|---|---|---|---|---|---|---|---|---|
| | Youth-ankle Dataset | | | | | | | | |
| | Subject-8 (Minimum) | | | Subject-12 (Maximum) | | | Subject-19 (Median) | | |
| 10 | 83.53 ± 11.52 | 56.06 ± 10.62 | 58.87 | 96.46 ± 1.57 | 66.24 ± 11.21 | 95.88 | 84.99 ± 6.02 | 72.10 ± 6.72 | 89.14 |
| 25 | 89.18 ± 6.07 | 70.69 ± 5.85 | | 96.89 ± 1.85 | 83.20 ± 6.57 | | 89.79 ± 4.01 | 81.12 ± 5.62 | |
| 50 | 92.97 ± 6.74 | 78.31 ± 0.48 | | 96.91 ± 2.92 | 85.05 ± 10.93 | | 90.30 ± 3.96 | 84.57 ± 0.93 | |
| 75 | 96.39 ± 5.24 | 79.70 ± 1.85 | | 97 ± 4.76 | 87.78 ± 6.10 | | 95.50 ± 5.1 | 87.13 ± 0.84 | |
| 90 | 98.33 ± 2.99 | 80.28 ± 6.48 | | 98.29 ± 2.56 | 89.07 ± 3.90 | | 97.83 ± 4.38 | 84.19 ± 7.09 | |
| | Youth-wrist Dataset | | | | | | | | |
| | Subject-3 (Minimum) | | | Subject-20 (Maximum) | | | Subject-11 (Median) | | |
| 10 | 89.37 ± 5.54 | 74.76 ± 4.84 | 78.21 | 97.50 ± 1.14 | 84.52 ± 3.90 | 95.56 | 92.29 ± 1.21 | 70.29 ± 4.92 | 90.2 |
| 25 | 91.73 ± 4.82 | 84.88 ± 3.18 | | 98.10 ± 1.32 | 87.66 ± 3.53 | | 94.43 ± 2.68 | 80.06 ± 6.35 | |
| 50 | 91.96 ± 10.52 | 90.46 ± 5.03 | | 98.01 ± 2.81 | 92.31 ± 0.37 | | 92.71 ± 8.91 | 90.20 ± 0.14 | |
| 75 | 93.80 ± 8.66 | 88.98 ± 3.62 | | 99.16 ± 1.69 | 92.87 ± 3.04 | | 95.19 ± 9.62 | 90.20 ± 2.74 | |
| 90 | 98.86 ± 3.61 | 91.12 ± 5.59 | | 99.17 ± 1.84 | 92.57 ± 5.29 | | 96.75 ± 8.59 | 92.27 ± 7.05 | |

Figure 18:
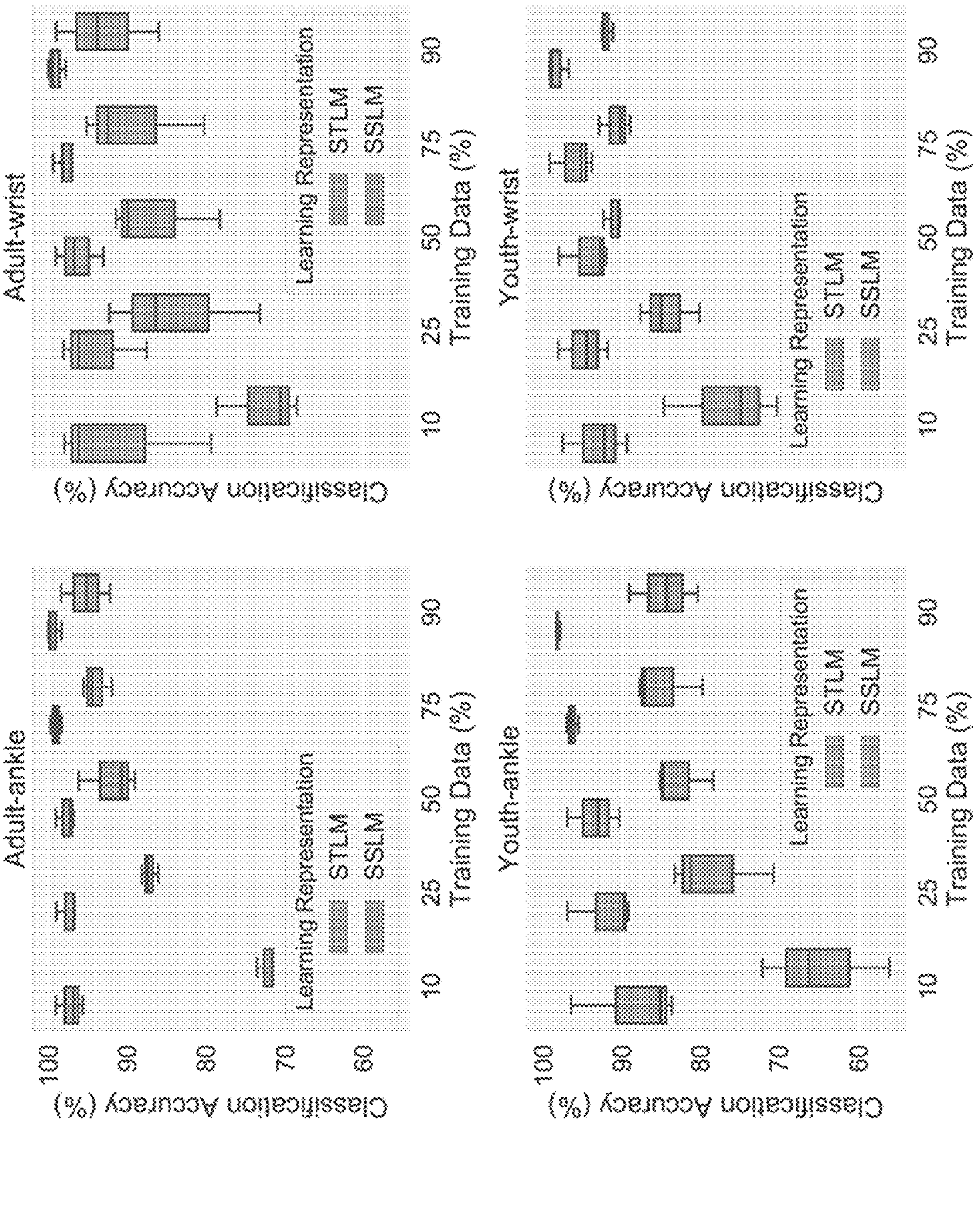
FIG. 18 illustrates boxplot distributions for the classification accuracies of STLM and SSLM for the outlier subjects on four datasets for a better statistical comparison according to some embodiments.

The advantages of sub-transfer learning using previous experience from training on other subjects become apparent when the inventors compared the classification performance of this learning representation with the subject-specific learning with no prior training. The inventors observed that in most instances especially for the subjects with the lowest accuracies, STLM provides a significant boost to the classification accuracy compared to both SM & SSLM. When the subject specific accuracies are already good or median, the sub-transfer learning still provides a better performance albeit less so when compared to the SM. Statistically speaking (more on this in the next subsection), statistically significant differences can be found when the accuracy is low, but not when the accuracy is high. More importantly, these gains in performance are realized only when using a very small percentage of the subject specific samples (i.e., 10% which generally means around 10 to 15 samples per subject) where SSLM fails to compete with either approach. For the adult-wrist dataset, the most difficult dataset in this study based on all previously published [?] results, STLM outperforms SM with LOSO by a significant margin (almost 80% compared to 66%) for the lowest accuracy subject 6, a robust margin (98% to 91%) for the median accuracy subject 33 while having the same performance for the subject where the accuracy is already very high (96% in both cases) even when using only 10% of the samples from the test set. Interestingly, SSLM displays a competitive performance with the SM for the lowest accuracy subjects, which highlights the insufficiency of a large model trained on the general population on outlier subjects. For these instances, subject-specific training has its own advantages as it is a much less resource-intensive way to train the learning algorithm on a specific subject with associated trade-offs in accuracy. FIG. 18 displays the boxplot distributions for the classification accuracies of STLM and SSLM for the outlier subjects on four datasets for a better statistical comparison.

To compare the statistical significance of the performance of a proposed model compared to the SM and SSLM, the inventors conducted a statistical hypothesis test using the Wilcoxon signed-rank test. To perform any statistical test, the inventors should investigate the independence of the observations, the homogeneity of the variance and the normality of the data tests to make common assumptions about the experimental data which constitutes the average classification accuracies of the STLM, SSLM and SM models on the 10% train data. Since the distributions of classification rates for these three models do not necessarily satisfy the above assumptions for a standard statistical significance test, the inventors applied a popular non-parametric approach using a Wilcoxon signed-rank test for paired data. For two groups of dependent paired data, the Wilcoxon signed-rank test ranks the absolute values of the differences between the paired observations and realizes whether the two dependent samples are chosen from populations having the same distribution.

TABLE 11

Statistical significance analysis between the performances of the learning representations on twelve subjects of four datasets

| Model | Null Hypothesis (h) | p-value (p) | Interpretation |
|---|---|---|---|
| SM vs. STLM | 1 | 0.0093 | Significant |
| STLM vs. SSLM | 1 | 4.88E−04 | Significant |
| SM vs. SSLM | 1 | 9.77E−04 | Significant |

Table 11 shows that for the Wilcoxon signed-rank test, the null hypotheses (h) are statistically rejected in case of every paired comparison. Since the average classification accuracies of STLM>SM>SSLM, it can be concluded that the STLM is statistically significantly better than SM which in turn is better than SSLM.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A system for human activity recognition, comprising:

a memory; and a processor communicatively coupled to the memory;

wherein the memory stores a set of instructions which, when executed by the processor, cause the processor to:

obtain a trained two-dimensional convolutional neural network (2D-CNN) deep learning model;

obtain a plurality of training two-dimensional frequency domain data samples for a user;

generate a plurality of synthetic training two-dimensional frequency domain data samples for the user;

update the trained 2D-CNN deep learning model based on the plurality of training two-dimensional frequency domain data samples and the plurality of synthetic training two-dimensional frequency domain data samples;

obtain raw sensor data for the user from at least one wearable motion sensor positioned on a body part of the user, the raw sensor data comprising single-axis temporal acceleration data for a spatial axis that provides a largest dynamic range of motion among three spatial axes;

resample the raw sensor data at a uniform fixed rate;

filter the resampled raw sensor data using a lowpass filter with a cut-off frequency configured to eliminate non-motion noise from the resampled raw sensor data;

generate two-dimensional frequency domain spectrotemporal representation data corresponding to the filtered resampled raw sensor data;

apply the two-dimensional frequency domain spectrotemporal representation data to the updated trained 2D-CNN deep learning model;

receive a classification indication from the updated 2D-CNN-trained 2D-CNN deep learning model;

provide a human activity indication of the user based on the classification indication; and output the human activity indication of the user to a display.

2. The system of claim 1, wherein the updated trained 2D-CNN deep learning model comprises: a first two-dimensional convolution layer with a first activation function and a second two-dimensional convolution layer with a second activation function to extract a feature map.

3. The system of claim 2, wherein each of the first two-dimensional convolution layer with the first activation function and the second two-dimensional convolution layer with the second activation function performs a convolution operation with 64 filters of kernel size of (5, 5).

4. The system of claim 2, wherein the updated trained 2D-CNN deep learning model further comprises: a first max pooling layer and a second max pooling layer to compute maximum information from the feature map, the first max pooling layer being between the first two-dimensional convolution layer with the first activation function and the second two-dimensional convolution layer with the second activation function, a second max pooling layer being coupled with the second two-dimensional convolution layer with the second activation function.

5. The system of claim 4, wherein the updated trained 2D-CNN deep learning model further comprises:

a fully connected layer configured to receive the maximum information from the feature map; and an output layer coupled to the fully connected layer, the output layer being configured to produce the classification indication.

6. The system of claim 1, wherein the classification indication is one of four classification indications.

7. The system of claim 1, wherein the classification indication corresponds to an ambulation indication, a cycling indication, a sedentary indication, or an others indication.

8. The system of claim 1, wherein the set of instructions, when executed by the processor, further causes the processor to preprocess the raw sensor data by resampling non-uniformly sampled raw sensor data at a uniform fixed rate and low-pass filtering the resampled raw sensor data to limit bandwidth and reduce non-motion noise prior to generating the spectrotemporal representation data.

9. The system of claim 1, wherein the trained 2D-CNN deep learning model comprises a source model trained using leave-one-subject-out (LOSO) cross-validation on training data from a plurality of subjects such that raw sensor data from the user is excluded from training the source model and reserved for the plurality of training two-dimensional frequency domain data samples for the user used to update the trained 2D-CNN deep learning model.

10. The system of claim 1, wherein the raw sensor data comprises a plurality of time-domain observations for the user, and wherein the plurality of training two-dimensional frequency domain data samples for the user comprise two-dimensional frequency domain spectrotemporal representation data generated from the plurality of time-domain observations after randomly shuffling an order of the plurality of time-domain observations.

11. The system of claim 1, wherein the set of instructions, when executed by the processor, further causes the processor to:

receive a user-provided activity input indicating a human activity that differs from the human activity indication provided by the updated trained 2D-CNN deep learning model; and further tune the updated trained 2D-CNN deep learning model in a semi-supervised manner using the user-provided activity input as a ground truth label.

12. A system for deep learning model training for human activity recognition, comprising:

a memory; and a processor communicatively coupled to the memory;

wherein the memory stores a set of instructions which, when executed by the processor, cause the processor to:

obtain a plurality of raw sensor training datasets obtained from at least one subject wearing a wearable motion sensor, the raw sensor data comprising single-axis temporal acceleration data for a spatial axis that provides a largest dynamic range of motion among three spatial axes;

resample the raw sensor training datasets at a uniform fixed rate;

filter the resampled raw sensor datasets using a lowpass filter with a cut-off frequency configured to eliminate non-motion noise from the resampled raw sensor datasets;

generate a plurality of two-dimensional frequency domain spectrotemporal representation training datasets based on the plurality of filtered resampled raw sensor training datasets;

train a two-dimensional convolutional neural network (2D-CNN) deep learning model based on the plurality of two-dimensional frequency domain spectrotemporal representation training datasets to classify the plurality of two-dimensional frequency domain spectrotemporal representation training datasets into a plurality of classification indications using leave-one-subject-out (LOSO) cross-validation with a random shuffle, wherein for each fold of the LOSO cross-validation, training data comprises two-dimensional frequency domain spectrotemporal representation datasets from all subjects except a designated user, and test data comprises two-dimensional frequency domain spectrotemporal representation datasets from the held-out subject;

obtain a plurality of training two-dimensional frequency domain data samples for the user;

generate a plurality of synthetic training two-dimensional frequency domain data samples for the user;

update the trained 2D-CNN deep learning model based on the plurality of training two-dimensional frequency domain data samples and the plurality of synthetic training two-dimensional frequency domain data samples; and store the updated trained 2D-CNN deep learning model to provide a human activity indication of the user.

13. The system of claim 12, wherein the set of instructions, when executed by the processor, further causes the processor to: generate the plurality of synthetic training two-dimensional frequency domain data samples for the user directed to a first classification indication of the plurality of classification indications, a first amount of datasets in the first classification indication being smaller than a second amount of datasets in another classification indication of the plurality of classification indications.

14. The system of claim 13, wherein at least a subset of the plurality of synthetic training two-dimensional frequency domain data samples for the user are generated with interpolation between two non-synthetic two-dimensional frequency domain spectrotemporal datasets in the plurality of spectrotemporal representation training datasets, and wherein the two non-synthetic spectrotemporal datasets are in the first classification indication.

15. The system of claim 12, wherein the 2D-CNN deep learning model is an unsupervised deep learning model.

16. The system of claim 12, wherein the plurality of classification indications corresponds to an ambulation indication, a cycling indication, a sedentary indication, and an others indication.

17. The system of claim 12, wherein the plurality of raw sensor training datasets comprises a plurality of time-domain observations, and wherein generating the plurality of two-dimensional frequency domain spectrotemporal representation training datasets comprises randomly shuffling an order of the plurality of time-domain observations and generating, from the plurality of time-domain observations, a plurality of two-dimensional frequency domain spectrotemporal representation observations that form the plurality of two-dimensional frequency domain spectrotemporal representation training datasets.

* * * * *